US012712076B1

(12) United States Patent
Park et al.

(10) Patent No.: US 12,712,076 B1
(45) Date of Patent: *Aug. 18, 2026

(54) DECISION SUPPORT PLATFORM

(71) Applicant: Cardinal Health Commercial Technologies, LLC, Dublin, OH (US)

(72) Inventors: Tanya Park, Dublin, OH (US); Sandeep Gulati, Dublin, OH (US); Graham Burks, Dublin, OH (US); Pravin Rane, Dublin, OH (US); Steven Jensen, Dublin, OH (US); Amy Valley, Columbus, OH (US)

(73) Assignee: Cardinal Health Commercial Technologies, LLC, Dublin, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/921,985

(22) Filed: Oct. 21, 2024

Related U.S. Application Data

(63) Continuation of application No. 17/581,563, filed on Jan. 21, 2022, now Pat. No. 12,148,528.

(Continued)

(51) Int. Cl.
*G16H 40/67* (2018.01)
*G16H 10/60* (2018.01)
(Continued)

(52) U.S. Cl.
CPC ............. *G16H 40/67* (2018.01); *G16H 10/60* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | | |
|---|---|---|---|
| 8,917,272 | B2 | 12/2014 | Regan et al. |
| 10,622,105 | B2 | 4/2020 | Von Reden |

(Continued)

FOREIGN PATENT DOCUMENTS

| | | | |
|---|---|---|---|
| WO | 2020/227169 | A1 | 11/2020 |

OTHER PUBLICATIONS

Hawley et al. ("The impact of the format of graphical presentation on health-related knowledge and treatment choices." Patient education and counseling 73.3 (2008): 448-455) (Year: 2008).*

(Continued)

*Primary Examiner* — Christopher B Tokarczyk
(74) *Attorney, Agent, or Firm* — ArentFox Schiff LLP

(57) ABSTRACT

A medical decision system is implemented as a computer platform that extracts electronic medical record information associated with a patient receiving medical care. The platform also outputs a graphical user interface that facilitates navigation by a user, of an electronic guideline selected based upon an identification of the patient receiving medical care or selected information from the extracted electronic medical record information. Moreover, the platform stores a value for a tuning parameter that affects clinical decision making. Also, the platform generates a customized, clinical pathway for the patient receiving medical care using the value of the tuning parameter, where the generated clinical pathway recommends a future clinical service for the patient receiving medical care, and the clinical pathway is reconciled with actual costs of care extracted from electronically retrieved cost information. Yet further, the platform outputs to a first display screen, the generated clinical pathway.

23 Claims, 11 Drawing Sheets

Related U.S. Application Data

(60) Provisional application No. 63/140,717, filed on Jan. 22, 2021.

(51) Int. Cl.
*G16H 50/20* (2018.01)
*G16H 50/30* (2018.01)

(56) References Cited

U.S. PATENT DOCUMENTS

| | | | | |
|---|---|---|---|---|
| 10,687,705 | B2 | 6/2020 | Dirghangi et al. | |
| 10,777,321 | B2 | 9/2020 | Shetty et al. | |
| 10,789,266 | B2 | 9/2020 | Bhabesh et al. | |
| 10,791,930 | B2 | 10/2020 | Soyao et al. | |
| 2016/0012189 | A1 | 1/2016 | Farha et al. | |
| 2016/0092641 | A1* | 3/2016 | Delaney | G16H 40/20 705/3 |
| 2017/0169171 | A1* | 6/2017 | Loeb | G16H 20/40 |
| 2017/0169173 | A1* | 6/2017 | Snow, Jr. | G16H 40/20 |
| 2018/0157799 | A1* | 6/2018 | Ketterer | G16H 10/60 |
| 2019/0013094 | A1 | 1/2019 | Johnson | |
| 2019/0051392 | A1 | 2/2019 | Givoly et al. | |
| 2020/0234826 | A1 | 7/2020 | Said | |
| 2020/0273578 | A1 | 8/2020 | Kutzko et al. | |
| 2020/0342375 | A1 | 10/2020 | Rubin et al. | |
| 2020/0350044 | A1 | 11/2020 | St. Clair et al. | |
| 2020/0357521 | A1 | 11/2020 | Baker | |

OTHER PUBLICATIONS

"CHSS Provider Office Value-Based Care (VBC) Solutions VBC Care Tracker Project", Innovation Acceleration Team (IAT) Review, Cardinal Health, Sep. 11, 2020.

"Breast Cancer", NCCN Clinical Practice Guidelines in Oncology (NCCN Guidelines, Version 6.2020, Sep. 8, 2020 (Part 1, pp. 1-ST-7).

"VBC Care Tracker—Intellectual Protection Discussions", Meeting 1: Oct. 28, 2020, and Meeting 2: Nov. 23, 2020.

"CAH's Value-Based Care Solution Offering: VBC: Care Tracker", May 8, 2020.

"Value-Based Care Solutions (Strategy Activation Project)" document.

"NCCN Guideline: Treatment by Cancer Type", National Comprehensive Cancer Network, https://www.nccn.org/guidelines/category_1, retrieved Jan. 25, 2022.

"Clinical Practice Guidelines", American College of Rheumatology, https://www.rheumatology.org/Practice-Quality/Clinical-Support/Clinical-Practice-Guidelines, retrieved Jan. 25, 2022.

"Breast Cancer", NCCN Clinical Practice Guidelines in Oncology (NCCN Guidelines, Version 6.2020, Sep. 8, 2020 (Part 2, pp. ST8-MS-46).

"Breast Cancer", NCCN Clinical Practice Guidelines in Oncology (NCCN Guidelines, Version 6.2020, Sep. 8, 2020 (Part 3, pp. MS-47-MS-95).

"Breast Cancer", NCCN Clinical Practice Guidelines in Oncology (NCCN Guidelines, Version 6.2020, Sep. 8, 2020 (Part 4, pp. MS-96-MS-135).

* cited by examiner

DECISION SUPPORT PLATFORM

CROSS REFERENCE TO RELATED APPLICATIONS

This application is a continuation application of U.S. patent application Ser. No. 17/581,563, filed Jan. 21, 2022, having the title "POINT-OF-CARE CLINICAL DECISION SUPPORT PLATFORM" now allowed, which claims the benefit of U.S.

Provisional Patent Application Ser. No. 63/140,717, filed Jan. 22, 2021, having the title "POINT-OF-CARE CLINICAL DECISION SUPPORT PLATFORM", the disclosures both of which are incorporated herein by reference in their entirety.

BACKGROUND

The present disclosure relates in general to a clinical decision support platform, and more particularly, to an extensible, point-of-care clinical decision support platform.

Modern medicine has brought about an ever-increasing number of treatment options to address medical conditions such as diseases, disorders, physiological conditions, etc. However, the improvements in medical care have also increased the complexity of care, the number of choices available for care, and a widening range of cost options to address care. Because of the depth and complexity of care options available, it is possible that an individual receives care that does not align with an optimal care plan for that individual.

BRIEF SUMMARY

According to various aspects of the present disclosure, a medical decision system is provided. The system comprises a platform that carries out program code to extract electronic medical record information associated with a patient receiving medical care. The platform further carries out program code to output a graphical user interface that facilitates navigation by a user, of an electronic guideline, where the electronic guideline is selected based upon at least one of an identification of the patient receiving medical care or selected information from the extracted electronic medical record information. Moreover, the platform carries out program code to store a value for a tuning parameter that affects clinical decision making, where the value for the tuning parameter is determined based upon at least one of: the identification of the patient receiving medical care, the extracted electronic medical record information, or information extracted from the electronic guideline. Still further, the platform carries out program code to generate a customized, clinical pathway for the patient receiving medical care using the value of the tuning parameter, wherein the generated clinical pathway recommends a future clinical service for the patient receiving medical care, and the clinical pathway is reconciled with actual costs of care extracted from electronically retrieved cost information. Correspondingly, the platform carries out program code to output to a first display screen, the generated clinical pathway.

According to further aspects of the present disclosure herein, a computer-implemented process is provided, for building a care plan that is customized for a patient receiving medical care. The process comprises extracting electronic medical record information associated with the patient receiving medical care. The process also comprises outputting a graphical user interface that facilitates navigation by a user, of an electronic guideline, the electronic guideline selected based upon at least one of an identification of the patient receiving medical care or selected information from the extracted electronic medical record information. Moreover, the process comprises storing a value for a tuning parameter that affects clinical decision making, where the value for the tuning parameter is determined based upon at least one of: the identification of the patient receiving medical care, the extracted electronic medical record information, or information extracted from the electronic guideline. Also, the process comprises generating a clinical pathway for the patient receiving medical care using the value of the tuning parameter to custom tailor the care plan for the patient receiving medical care. In this regard, the generated clinical pathway recommends a future clinical service for the patient receiving medical care. Also, the clinical pathway is reconciled with actual costs of care extracted from electronically retrieved cost information. The process further comprises conveying an output that characterizes the generated clinical pathway.

DETAILED DESCRIPTION

According to various aspects of the present disclosure, a computer-implemented point-of-care clinical decision support platform is provided, which tracks patient care over time. In particular, aspects herein provide a computer-implemented point-of-care clinical decision support platform that improves upon conventional patient tracking software by utilizing a core platform that can be expanded using an extensible application programming interface (API) architecture. The extensible API architecture enables expansion, updating, modification, adaptation, customization, etc., of the core platform using capabilities from native as well as third-party resources. This allows adaptation to different clinical practices, selection of best-in-class resources, customization in adherence to guidelines, etc. Thus, the extensible API architecture allows the core platform to adapt to the workflows, preferences, and existing tools of medical care providers.

According to further aspects of the present disclosure, systems and processes are provided that convert guidelines into electronic navigable interactive guidelines that provide numerous technical advantages over existing systems. Conventional practice requires clinicians to find, download and read complex guidelines for treating patients. These guidelines are often unstructured and difficult to navigate. However, aspects herein transform the unstructured and lengthy guidelines into an electronic model that is visually organized and interactively navigable. The navigable nature of the interactive guideline provides significant improvements over mere digitalization. Here, the ability to navigate the interactive guideline means that clinicians can carefully track and follow guideline paths, save, reload, resume, track, and otherwise leverage the guideline in a manner not otherwise possible with a paper or electronic unstructured document, as will be described in greater detail herein.

Moreover, conventional clinical processes are rigid and can result in a patient receiving care in a non-optimized manner. However, a point-of-care clinical decision support platform is provided herein that is tunable so that clinical decisions can be made and assessed by tuning specific parameters so that the platform accounts for specific patient information and adapts that patient information to a care plan that can be custom tailored for the individual receiving care. Particularly, this flexible platform allows clinicians to performance tune a clinical progression based upon a number of factors, as set out in greater detail herein.

Example Point-of-Care Clinical Decision Support Platform

Figure 1:
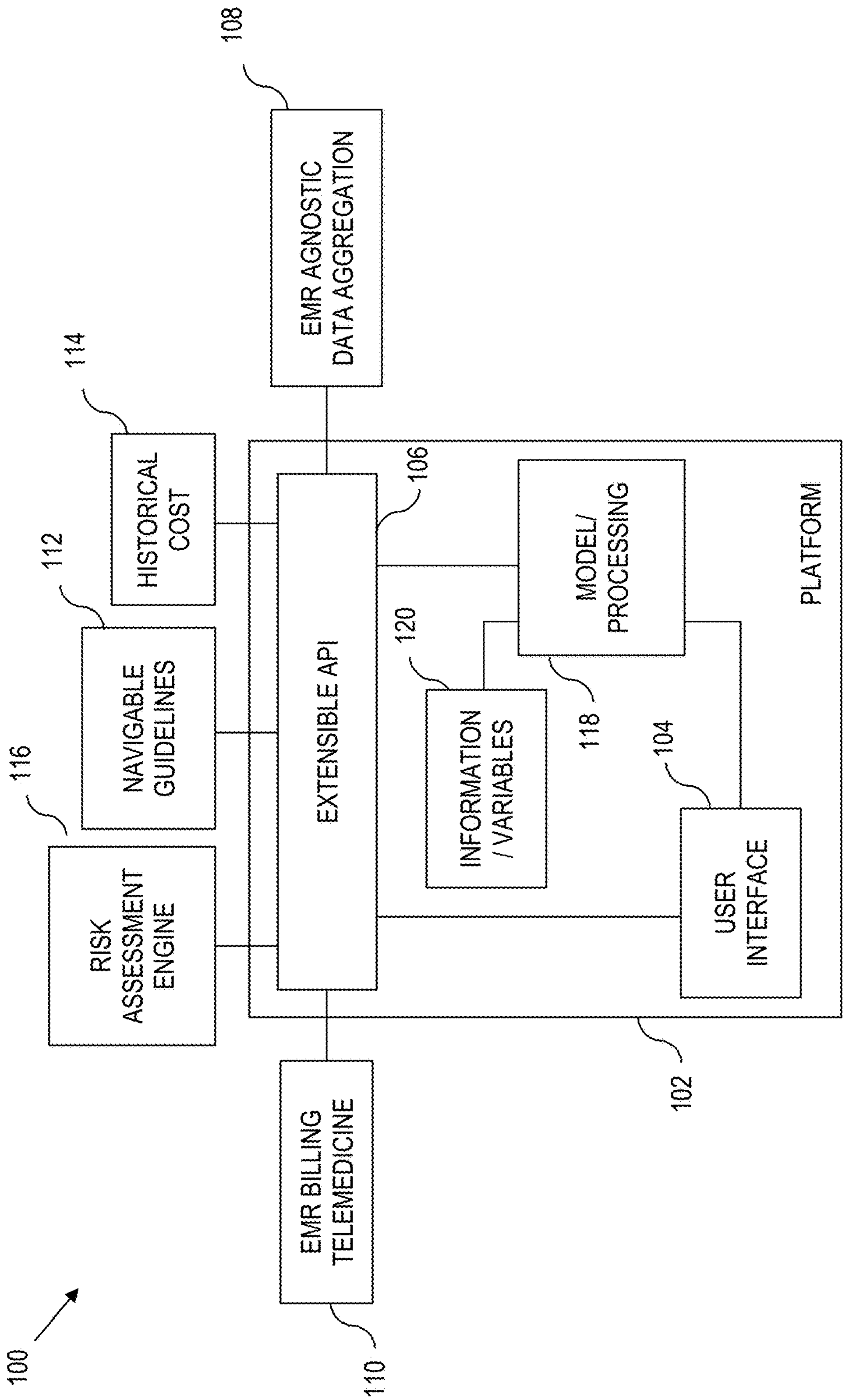
FIG. 1 is a block diagram illustrating a point-of-care clinical decision support platform, according to various aspects of the present disclosure.

Turning now to the drawings, and in particular, to FIG. 1, a block diagram 100 illustrates a platform 102 for a point-of-care medical decision system. The platform 102 includes a user interface 104 that allows a user (e.g., a physician, nurse, other medical staff, etc.) to enter information, to control the platform 102, or both. The user interface 104 also supplies information to the user. In some embodiments, the user interface 102 is a graphical user interface 104 that provides a graphical environment for the display of information to the user, and for interfacing with the user to obtain inputs, commands, and to otherwise facilitate user interaction.

The illustrated platform 102 further includes an extensible application programming interface (API) component 106 that can be coupled to native and/or third-party applications that provide information, a service, or both to the platform 102. For example, an add-on application may comprise an electronic medical record (EMR) aggregator 108. As another example, an add-on application may comprise a telemedicine application 110 that can feed clinical EMR data to the platform 102. In this regard, in some embodiments, the system provides an open platform solution that can bring together data, insights, processing, decision support, analytics, etc., into a centralized system. The integration of resources from the open platform enables capabilities that any add-on or third party solution on its own would be unable to provide. For instance, the illustrated platform 102 is particularly well suited to drive/improve patient care, reduce cost to the affected patients, reduce time and/or cost to the clinician, and improve the consistency of patient care.

As still another example, an add-on application can comprise a navigable guideline application 112. The navigable guideline application 112 can interact with one or more data sources to enable navigation through guidelines (e.g., guidelines provided by the National Comprehensive Cancer Network (NCCN), American Society of Clinical Oncology (ASCO), European Society for Medical Oncology (ESMO), a payer guideline, insurance guideline, other guideline, combinations thereof, etc.). For example, the NCCN (and others) provides guidelines associated with medical treatments. The navigable guideline application 112 converts, transforms, adapts, or otherwise provides such guidelines in an electronic, graphical, navigable form, as set out in greater detail herein.

In some embodiments, the navigable guideline application 112 can facilitate navigating a single guideline. In other embodiments, a clinical pathway for a patient may trigger the platform via the navigable guideline application 112 to utilize multiple guidelines. Here, the various integrated guidelines can be derived from the same source (e.g., NCCN) or from a combination of sources (e.g., a combination of NCCN, ASCO, ESMO, payer guideline, insurance carrier guideline, localized guideline, etc.). The use of electronic, navigable versions of the guidelines with the platform 102 is discussed in greater detail herein.

Yet another example add-on application can comprise a historical cost application 114 that supplies historical information regarding different treatment plans, where the cost can be financial cost, time cost, etc.

Moreover, an add-on application can comprise a risk assessment engine 116. For instance, in an example embodiment, the risk assessment engine 116 provides recommendations of interventions based on risk. Other native and/or third-party applications may also be used.

In example embodiments, the API component 106 is extensible. As such, the platform 102 can reconfigure itself or is otherwise reconfigurable, such as by adding appropriate interfaces via the API component 106. Such a process enables applications to be added to a core of the platform 102 in a scalable manner. In this regard, not all of the applications listed above (108, 110, 112, 114, 116) must be used. For example, the platform 102 may utilize no add-on applications or any number of applications so long as an appropriate API is available. As another example, a given implementation of the platform 102 can utilize different applications than those identified above, e.g., by implementing an appropriate interface in the extensible API component 106.

In some embodiments, a user may set a tuning parameter (or multiple tuning parameters) via the user interface 104. Each tuning parameter may be utilized, for example, to assist a clinician in suggesting, recommending, automatically generating, combinations thereof, etc., one or more clinical pathways associated with a corresponding patient. Here, the tuning parameter is utilized by the platform 102 to performance tune a clinical pathway.

As an initial example, because the extensible API component 106 aggregates information, e.g., from internal resources, from external resources, from one or more of the available add-on applications, combinations thereof, etc., content can be combined, shared, modified and manipulated across the platform 102 and components thereof. Thus, as an illustrative example, the platform 102 can include an API component for cost information 114. As discussed above, the cost may be time-related costs, financial-related costs, etc. In some embodiments, a user may set a tuning parameter (or multiple tuning parameters) via the user interface 104 that is associated with a cost suited to the patient. Thus, time, dollars, a combination of monetary expenses per unit of time, etc., can be factored into the clinical pathway.

In some embodiments, a tuning parameter can affect decision making based upon cost in terms of real-time cost, individualized cost to a target (or targets), based upon total treatment, treatment for a period (month, quarter, year, etc.), cost for a particular treatment, cost for a next step in treatment, or any other desired level of granularity. Thus, aspects herein can provide visibility into the performance of proactive efforts and the real-time impact on costs of care. Moreover, aspects herein can include individualized cost of care calculation by patient, cost tracking towards a target, or combinations thereof. Additionally, the platform can track the total cost of care for the individual patient, which can be reconciled and modified, even dynamically, using the tuning parameter. The platform can also analyze the data/information available to come up with an estimate/prediction of the total cost of care for the patient being treated as well as predict cost changes based on diversions in treatment regimens, thus tracking total cost of care and tracking progression (costs) as estimated/predicted at start of treatment. This allows tuning, via the tuning parameter(s), even over time, to account for dynamic changing conditions, treatments, patient progressions, etc. This also allows modeling of possible outcomes based upon modifications to tuning parameters.

As another example, cost can be set, targets can be assigned (for total care, care over a window, care over a treatment, care over a regimen, etc.), and a care plan can be tuned as a function of progression through a guideline, e.g., via the navigable guidelines 112. As yet another example, medical records regarding a patient can be extracted and mapped to a guideline along with cost information, thus pulling from multiple add-on applications to perform a clinical pathway process that is tuned to a value-based care algorithm. Thus, the extensible API component 106 can be expanded to support any number of native and/or third-party applications (e.g., multiple cost databases, multiple EMR databases, multiple guideline databases, multiple risk assessment engines, etc., and combinations thereof).

The platform 102 can optionally further comprise a model component 118. The model component facilitates tuning of patient care, and can be utilized to define models, algorithms, workflows, etc. In this regard, a model can be created that is expressed as a set of rules processed by a rules engine, a state machine, a machine learning algorithm, artificial intelligence, a recommender engine, a statistical and/or algorithmic model processor, any combination thereof, etc.

For instance, the model component 118 can be used to generate a clinical pathway based on information gathered through the extensible API component 106, where the clinical pathway recommends a future clinical service. In some embodiments, the recommended future clinical service is reconciled with actual costs (e.g., based on a default tuning parameter or a tuning parameter chosen by the user). In several embodiments, the model component 118 can utilize the navigable guidelines 112, e.g., guidelines set by medical professionals (e.g., the NCCN guidelines, ESMO guidelines, ASCO guidelines, payer guidelines, combinations thereof).

In various embodiments, a clinician may decide to use the model component 118 to organize patient care such that patient care follows a pathway defined by a guideline (i.e., strictly follow the guideline), and may even follow a static, pre-defined pathway, such as where the model component 118 is based on guidelines that do not change. In other embodiments, the clinician may decide to use the model component 118 such that patient care follows a pathway determined at least in part by patient factors and/or other external factors outside recommended guidelines. Yet further, the clinician may decide to use the model component 118 such that patient care can account for transitioning a patient out of or otherwise away from a guideline recommendation (e.g., to purse a pathway along the lines of a different guideline or other treatment plan—such as may be necessary due to changing medical condition, environmental factors, updated guidelines or best practices, etc.). In this regard, the clinician may decide to use the model component 118 such that patient care follows a pathway dependent upon one or more guidelines, independent of one or more guidelines, based upon feedback from patients that do not match up to guidelines, based upon feedback from patients that match to one or more guidelines, any other factor that the clinician determines to be informative to determining the patient's plan of care, combinations thereof, etc.

As such, as described more fully herein, use of one or more tuning parameters allows a clinician to "tune" a clinical pathway that is customized to the patient, balancing quality of care, cost, and other factors. Moreover, the use of the tuning parameters allows a clinician to ensure quality of care across multiple patients. For instance, the platform herein can use the tuning parameters to affect selection of biosimilars, as well as recommend alternative treatment regimes. For instance, selecting a given regimen, the platform can use guidelines and/or other resources described herein to present back all alternative treatments (or a prioritized list of alternative treatments, selected treatment options, etc.) that according to guidelines (or other resources leveraged herein), have similar outcomes for the patient. In some embodiments, cost is provided for each alternative. In some embodiments, alternatives are filtered based upon cost so that alternatives with similar cost are provided. Where at least one tuning parameter is cost, the alternative can be filtered to those options that satisfy criteria established by the cost (as well as other) tuning parameter(s).

In some embodiments, the model component 118 can facilitate dynamic processes, e.g., where the platform 102 queries a guideline database of electronically formatted navigable guidelines for updates, receives pushed updates from the guideline database, interacts with other add-on applications via the extensible API component 106, combinations thereof, etc.

Thus, workflows can be dynamically modified based on updates, e.g., from the guideline database, based upon the model itself updating an algorithm, due to changes in tuning parameter(s), due to changes in cost, due to changes in risk assessment, combinations thereof, etc.

Moreover, in some embodiments, a clinician interacting with the platform 102 triggers the model 118 to update/change a patient's clinical pathway based upon clinician interaction, inputs, modifications, etc. In other embodiments, the model 118 dynamically changes, e.g., based upon detecting updates, upon algorithm refinement, etc., or updates may occur as a result of a combination of clinician provided interactions and/or automated interactions.

In some embodiments (discussed herein), the platform 102 includes timestamp information that tracks patient progress. In some embodiments, the timestamps can help ensure that a patient stays on a treatment path, even in dynamic conditions. For instance, a timestamp can track not only time/date information, but also other metadata, e.g., the version number or revision of a guideline that the patient is progressing on. In this manner, a clinician can control patient care, e.g., to keep a patient on an existing clinical pathway for the patient, even where that pathway may be changed or deleted based on an update or new release of a guideline (e.g., by leveraging an archive guideline process as described in greater detail herein).

As discussed above, a clinical pathway can be based on the model component 118 and/or the information gathered through the extensible API component 106. However, the extensible API component 106 may have access to fewer third-party applications than required to supply the required information to create the clinical pathways. Therefore, in some embodiments, the platform 102 includes an information/variable process 120 that stores information, including variables, agreements, documents, and other resources needed by the platform 102. For instance, the platform 102 can utilize the information/variable process 120 to generate, impute, or otherwise establish values for select information that cannot be supplied via the extensible API component 106.

For example, the Centers for Medicare and Medicaid Services (CMS) (and other providers) make episode cost data available. However, such data is made available many months after episodes end. As such, data is typically not available while an episode is happening. Where a value-based care implementation is carried out, the platform 102 may leverage an add-on application via the API component 106 to attempt to obtain updated information, e.g., cost information. However, where such cost information is not available via an API call, then the system can opt to not show cost information. Alternatively, the system can extract information from the information/variables process 120, such as historical information that has previously been collected and stored, e.g., based upon CMS data that has been previously collected. Alternatively, the information/variables process 120 can synthesize values from stored historical data. As another example, a model generated by the model component 118 can utilize default values, e.g., stored or otherwise generated by the information/variables process 120. Thus, the model does not have to rely upon external resources to startup, run, or otherwise operate because base values can be stored and populated for one or more variables therein, internal to the platform 102. However, when information can be gathered from the extensible API component 106, any relevant default values can be overwritten with the gathered information.

In practical applications, the platform 102 is implemented by a computer, e.g., a server-based computer operating in a cloud environment. Here, a user may interact with the platform 102 by executing a browser or other client on a remote computer that communicates with the platform in the cloud computing environment. This architecture eliminates a requirement that add-on applications that interface with the platform 102 via the extensible API component 106 are co-located with the platform 102. Particularly, in practical applications, the add-on applications can exist in other locations accessible by the Internet, including being hosted on third-party servers. This allows the best add-on to be selected for a given application. This also allows add-ons to be changed, updated, etc., as noted more fully herein.

Patient Focused View and Practice Focused View Examples

By selecting appropriate add-on applications via the API interface 106, an implementation can select resources that fit into existing clinical practices and workflows, augmenting existing practices with tools that improve patient care, e.g., by including interfaces to any combination of medical information providers, medical/disease specialization resources, data aggregators, artificial intelligence, machine learning, and other risk assessment engines, cost analytic resources, guidelines, etc.

The flexibility of the extensible API also enables the platform to include a first interface that a clinician can use for patient-focused interactions. This first, patient focused view can enable the clinician to focus on patient care, manage cost of care for that patient, evaluate risks and interventions for a patient, evaluate patient demographics, etc. A second view can provide a practice-side view focused on practice level analytics, such as adherence by a physician to the guideline, evaluation of cost by population, to perform outlier identification, etc.

As a few illustrative examples of how the platform 102 can be used, assume that a clinician wants to model cost of care based upon episode cost. Aspects herein enable a clinician participating in value base care agreements to use the platform 102 to know the current cost of care during and after an episode of care so that the clinician can continually adjust care delivery to optimize for better care at lower cost.

In this regard, API features are provided in the extensible API component 106 to enable the clinician interacting through a client interface to be able to estimate practice cost of care for an episode based on medical condition (e.g., cancer type, etc.). The clinician is able to track practice cost during and after an episode. In some embodiments, the clinician is able to show practice cost in the decision support platform for a patient, and can categorize cost (drugs, visit (E&M), Labs etc.).

As yet another example, a GUI can be provided, e.g., via the user interface 104, model component 118, etc., that enables the clinician, interacting in a graphical environment within the platform 102 to find a cost of care that happens outside the practice in real time. For instance, a select capability can allow Medicare patients to share their data with a provider/vendor. Here, such information can be accessed via API calls.

In an example implementation of cancer care, when participating in an oncology care model (OCM), the client interface enables a clinician to be able to track the total cost of care for a patient episode in real time (including costs outside of the practice). As such, the clinician can be able to understand the current costs associated with a Medicare population and track if the care is performing/not performing. This is particularly helpful for OCM clients where clinicians may have target episode costs, they must hit.

As such, patient consent can be managed and patient claims can be pulled automatically, such as by using an API component 106 that interacts with an appropriate API, e.g., the "Blue Button" API of CMS. Once inside the platform 102, the model component 118 can classify pulled patient claim information into appropriate categories, such as Inpatient stays; ER, SNF, HH, Part D medications, etc.

A clinician can also use the clinical decision support platform to track a patient's progress as a function of adherence to an associated guideline and compare regimens. For instance, in an example of cancer care, a medical oncologist would be able to use the platform 102 to track patient progress/adherence to cancer-treatment guidelines and compare regimens, e.g., within the guideline based on data already in a regimen analyzer that is integrated into the platform 102 (e.g., via the model component 118, an extensible API call by the API component 106, combination thereof, etc.

When determining the right care for the patient, a clinician can search for a patient, review what's happened already and then take the next logical steps based on an appropriate guideline (or other resource) so that the clinician can give the patient the most accurate treatment possible. Thus, the clinician can see basic patient information (demographics). For a new patient, the clinician is able to search for a guideline and start navigating through the guideline. For any patient, the clinician is able to save progress through a guideline and is able to see a history and continue through guideline. The clinician can also freely navigate between patients and integrate with a regimen analyzer for regimen details. This allows the clinician to be able to compare regimens within a corresponding guideline.

In yet another illustrative example, the platform 102 can be utilized to generate an analytics summary for a practice covering all aspects of value based care.

When managing a practice and/or a practice's participation in value-based care agreements, a clinician has access to clear/easy to use analytics that summarize important key performance indicators (KPIs)/metrics related to value based care. The clinician can also gain visibility into good visualizations around outliers. In this regard, value based care agreements themselves can be made available to the platform 102, and may even be made available via the navigable guidelines component 112 so that a navigable care agreement can be factored with other navigable guidelines via a model generated by the model component 118 to create and/or customize a clinical pathway and define a path of care for a patient. In this regard, the user interface 104 can provide a graphical environment for the clinician to view and track the patient's progression, to reconcile actions at key steps, e.g., based upon value-based care, cost, clinical options, etc.

As such, the clinician can manage exceptions and also track overall performance of the practice with the scope of agreements. Moreover, the clinician can visualize/report/manage, evaluate total cost of care across an entire practice by medical care (e.g., cancer type), ensure adherence to guidelines, identify clear ways to get to outliers, etc. For instance, the clinician can evaluate patients that cost significantly more than other patients with the same cancer type and explore drivers that affect such outliers. The evaluation can also identify physicians that are not adherent to guidelines/pathways and provide attribution as to why. Moreover, the platform can provide the ability to show comparison to peers.

As noted above, in some embodiments, the platform 102, e.g., via the model component 118 can integrate an artificial intelligence (AI) and/or machine learning (ML) (collectively AI/ML) tool. As another example, AI/ML can be introduced via the API component 106 by connecting to an outside AI process to give clinicians insights along multiple clinical vectors for what actions the clinician should/could be taking with patients. Regardless of how implemented, this resource can provide augmented intelligence for a medical field (e.g., oncology).

By way of example, when managing a population of cancer patients, the clinician can interact with the AI interface via the API while remaining within the platform 102 to receive help figuring out what actions/interventions are needed to be taken and with which patients before they get worse so that the clinician can improve outcomes at lower cost. The AI engine can also provide attribution to explain why those interventions were suggested.

As a few practical additional examples, an AI API can assist the clinician to manage risk metrics such as a mortality risk, readmission risk, deterioration risk, avoidable admission risk, patient experience, mental health, etc., (where each risk can optionally be expressed in an associated, predefined time window, such as days, weeks, or other suitable time period).

In this regard, the extensibility of the platform 102 enables a myriad of permutations of uses, such as the ability to follow a patient care plan derived from navigating one or more guidelines. Another example capability is to enter and act upon non-guideline suggestions or actions for one or more patients. Another example capability is to compare and analyze patient populations to evaluate on-guideline vs off-guideline patient vectors, to compare differences in patient populations based upon different guidelines, different versions of a guideline, or other differences that can be identified by interacting with the platform. Yet further, example capabilities include the ability to generate by a controller of the platform 102, feedback to the clinician based upon patient data that does not match up with associated guideline(s), that does match up with associated guideline(s), or a combination thereof.

Notably, in some embodiments, the platform 102 serves as a wrapper handling the interface to add-on applications via the extensible API component 106, e.g., as an open platform integration engine. As such, a clinician can utilize one familiar interface and workflow and does not need to learn and understand how to connect to, use, and aggregate information from various cost, AI, medical information, guideline and other resources.

For instance, as described herein, in some embodiment, the platform 102 provides an open platform solution that facilitate integration of add-on application partners to facilitate electronic medical records (EMR) integration for access to clinical and financial data. The platform 102 can also provide access to preferred regimens and guidelines, as well as compliance monitoring. Indeed, in some embodiments, the guidelines are converted from unstructured documents into navigable models that significantly improve consistency, care, adherence to best practices, and reduced time and cost in following the guidelines. Yet further, the platform 102 can integrate therein, or integrate as an open platform communication with a third-party add-on, an AI-driven risk assessment engine and intervention component to enable a clinician to navigate not only risk evaluation, but also to identify interventions. Any combination of the above features can be layered with cost information, including historical cost information to provide a value-based care flow that optimizes care that is tuned to value-based parameters (e.g., time, money, etc.).

Moreover, because of the graphical user interface, dashboards, clinician screens, administrative screens, and optionally, client portal screens can be provided in a cohesive product. For instance, the model component 118 can execute a program presented to the clinician via the user interface 104, which equips a clinician with tools to manage patient population to improve quality of care and lower costs, identify patients including rising risk patients, triage high risk patients, provide decision support at the point of care, present regimen/formulary management (e.g., to pick lowest cost alternatives when available, etc.), provide analytics to aggregate data and provide insights, to track total cost of care, to track cost progression within a bundle, combinations thereof, etc.

In some embodiments, the model component 118 can create a holistic roadmap of a patient's treatment plan, including cost estimates that provide an alignment to clinical pathways and best practices guidelines. The dynamic nature of the platform 102 further enables updating a patient's roadmap in real-time (or at least near real time), e.g., by reconciling actual costs of care and clinical services with planned cost of care, and optionally with proactively recommended next steps with risks to the plan. Still further, the platform 102 can proactively recommend to patients, next steps with risks.

Because the platform 102 is network based, the platform 102 can also be used to benchmark patient care on a per clinician basis, per provider basis, per patent basis, per patient grouping basis, etc. The platform 102 can compute total cost of care for a patient, compare provider cost for the patient, compare provider cost for similar patients, recommend external providers, evaluate and benchmark total cost and incremental cost of care, etc. In this regard, the platform 102 can be utilized to implement an always-current care plan for patients, even amid changing patient conditions, amid changing guidelines, changing best practices, fluctuating cost, and amid changing treatment options. Patients can additionally access education, support resources, and see an up-to-date financial outlook, etc.

Notably, because the platform 102 can be leveraged by clinicians, decision Support (e.g., for selecting the preferred/optimized regimens and treatments) can be carried out at the point of care. Moreover, the platform 102 interacts with clinicians via monitoring. Thus, when a clinician selects an option, e.g., at the point of care, that is not in-line with a preferred regimen, the platform 102 can alert the clinician, provide the preferred regimen, accept deviations from the preferred regimen, learn why a clinical pathway was deviated, etc. The formulated management of the platform 102 allows the preferred regimen to be tuned, e.g., by balancing clinically optimal pathways, financially optimal pathways or a balance of clinical, financial, and optionally other considerations.

Example Process Using the Platform

Figure 2:
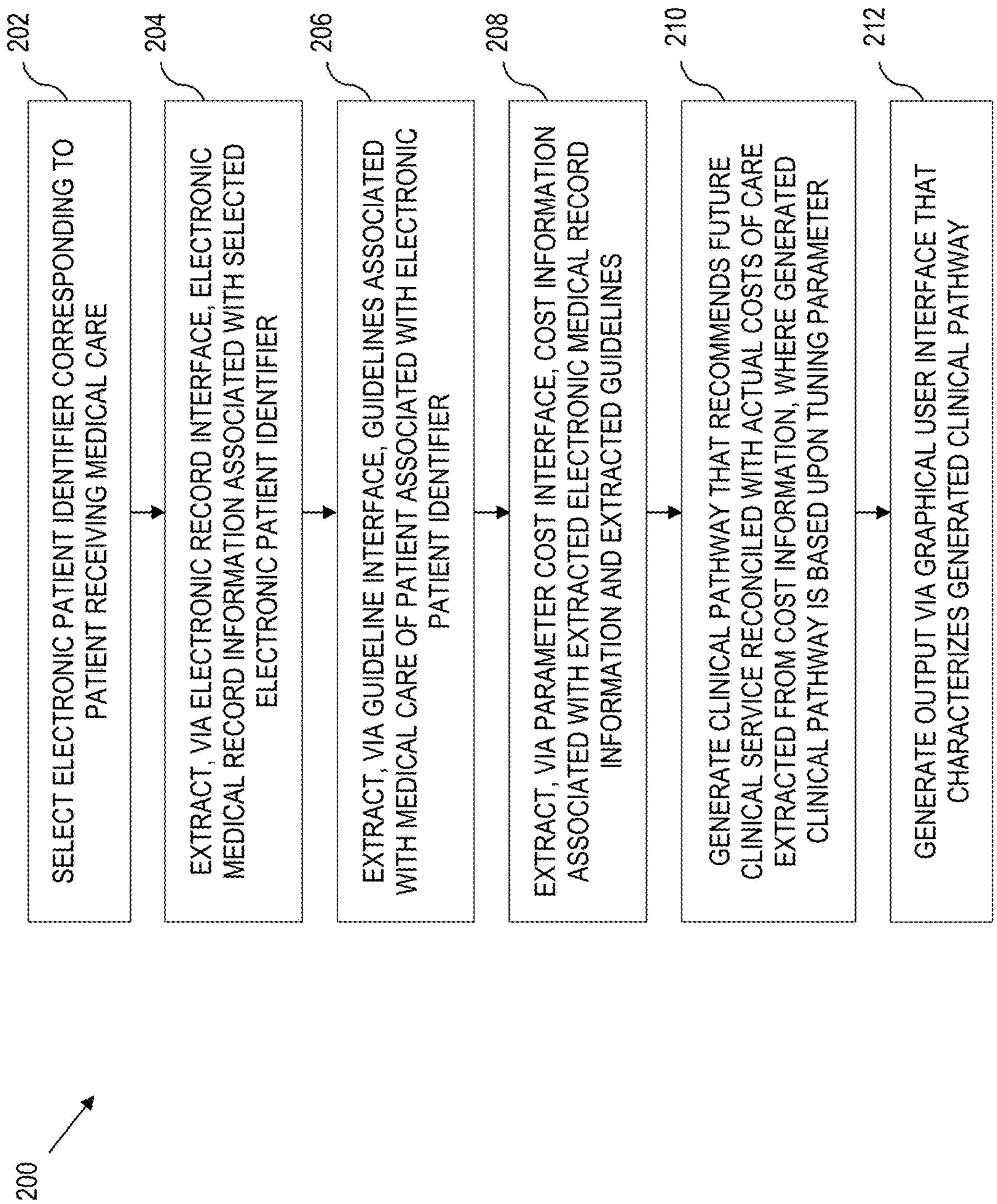
FIG. 2 is a flow chart illustrating a process for utilizing the point-of-care clinical decision support platform of FIG. 1.

Turning now to FIG. 2, a flow chart illustrates a process 200 for a point-of-care medical decision platform to illustrate an example of how to performance tune a clinical pathway. The process 200 may be performed by a computer system implementing the platform 102 and corresponding components described with reference to FIG. 1.

At 202, an electronic patient identifier corresponding to a patient receiving medical care is selected. The electronic patient identifier may be selected by receiving an indication of a patient identifier from the user through the user interface (102 of FIG. 1). Other ways to select the electronic patient identifier may be implemented as well (e.g., use a default, determine based on a schedule and a current time and date, etc.).

At 204, electronic medical record information associated with the electronic patient identifier is extracted via the electronic record interface. For example, the point-of-care medical decision system may be coupled to an electronic medical records database through the electronic record interface. When a patient is selected at 202, the system queries the electronic medical records database for records associated with the patient. The system then receives a response from the electronic medical records database and extracts electronic medical information from the response. For example, values for some of the variables of the model may be extracted from the response.

At 206, guidelines associated with medical care of the patient associated with the electronic patient identifier are extracted via a guideline interface. For example, if the patient is suffering from lung cancer, then the system queries the guidelines database for guidelines associated with lung cancer. The system then receives a response from the guidelines database and extracts guidelines from the response. As discussed herein, the guidelines may be used to create a dynamic or static model.

At 208, cost information associated with the extracted electronic medical record information and the extracted guidelines is obtained via a cost interface (e.g., an API to a historical cost database). The cost information can be associated with a performance tuning parameter that may be set by the user (e.g., via the user interface, as a default, etc.). For example, the tuning parameter may be a financial cost, a time cost, etc. In some embodiments, financial costs are broken into inside costs (i.e., costs associated with the user of the system) and outside costs (i.e., costs associated with entities separate from the user of the system).

Inside costs and outside costs may vary based on the user and/or the user's environment. For example, and not by way of limitation, a physician (user) that works for Hospital Network A may need to extract electronic medical record information for a patient. If the patient has already had medical services performed at Hospital Network A, then medical record information relating to those services, including financial costs, would likely be available to the physician through their association with Hospital Network A. Those financial costs would be considered "inside costs."

In addition to (or alternatively to) the medical services above, the patient may have had other medical services performed outside of Hospital Network A (e.g., medical services performed at Hospital Network B, visits to the emergency room (ER), elective surgeries at private practices, etc.). Analogously to the above, the financial costs from those outside medical services would be considered "outside costs" since they are external to Hospital Network A.

As noted in greater detail herein, in practical applications, other examples of tuning parameters that can be utilized to affect the generated clinical pathway include tuning parameters based upon cost, time, treatment, risk assessment, patient-profile similarity, patient profile differences, guidelines, a trajectory to transition an out-of-guideline patient into a guideline, or other factor that affects clinical decision making.

At 210, a clinical pathway is generated. The clinical pathway recommends a future clinical service reconciled with actual costs (e.g., time, financial, etc.) extracted from the cost information. For example, the system may recommend a future clinical service by interacting with the navigable guideline model to select the future clinical service as a node in the navigable guideline, as discussed herein. Further, the system can perform compliance monitoring of the patient by tracking progress of the patient relative to the generated clinical pathway.

At 212, the system generates an output for the user interface that characterizes the clinical pathway. In some embodiments, the output includes indica of a total predicted cost and how much of that total predicted cost has been used. In various embodiments, the output includes attributions of the total cost. For example, if a total cost is predicted to be $10,000 and two services have been performed for $2000 and $3000, then the output may include an indication that 50% of the costs have been used, and the first service used 20% of those costs and the second service used 30% of those costs. The predicted costs (including future costs) are based on the clinical pathway generated from the guidelines. Further, the output may include a prediction of future costs based upon detected changes representing a diversion in a treatment regimen defined by the generated clinical pathway.

With the system described herein, the platform can aid a user with decision support to help the user select preferred and optimized regimens and treatments at the point of care. Further, the system can aid the user in documenting the regimen and any deviations from a standard regimen (e.g., there may have been an updated model). This decision support is analyzed in the light of a tuning parameter (e.g., financial, time, etc.) to help to predict a total cost of care, and to help to predict possible changes in the costs in near real time as the patient progresses through the clinical pathway.

Navigable Interactive Guidelines

According to some embodiments of the present disclosure, the clinical decision support platform assists a care giver in matching a patient with an appropriate treatment based upon adherence to a specified guideline. Many diseases have clinical treatment guidelines aimed at helping physicians identify treatment options for patients, e.g., NCCN, ASCO, payer guidelines, etc., as set out in greater detail herein.

By way of non-limiting example, a computer system is provided, which presents a graphical user interface to a caregiver, e.g., a medical oncologist. The medical oncologist interacts with the graphical user interface in such a way that the patient, e.g., a cancer patient, is matched with patient care that follows an appropriate treatment based on adherence to a guideline, e.g., a National Comprehensive Cancer Network (NCCN) guideline. However, aspects herein are extensible to cover other guidelines.

Aspects herein also provide approaches that utilize technical computer program techniques to manipulate and generate new data types that transform unstructured and disparate data into linked navigable pathways that improve the performance of computer systems, computer displays, memory usage, and end user experiences. In some embodiments, the navigable pathways are graphical navigable pathways.

In this regard, graphical navigable pathways provide improved computer efficiency. In particular, loading a document such as an NCCN guideline, payer guideline, etc., can cause the computer to load a Portable Document Format (PDF) or other electronic document that could be hundreds of pages long. The graphical navigable view, however, collapses large amounts of text into a model that tracks a patient's progression according to the guideline. As such, the computer only needs to load small amounts of model data relevant to a current position and relevant pathways of the patient within the guideline. The model enables a visual presentation of relevant guideline parameters, while retaining the substance and integrity of the original guideline document. Moreover, the model can be navigable. This greatly increases the likelihood of guideline adherence because tracking over time becomes automated with no need to rely purely upon clinician manual efforts.

As such, the prior requirement of scrolling through hundreds of pages of unstructured information is greatly reduced or eliminated, resources consumed by searching is greatly reduced, user fatigue is reduced, and user screen time is reduced because the graphical visualization represents large amounts of data with concise visual metaphors.

Guideline Platform

According to aspects of the present disclosure, a guideline platform is provided, which can integrate with the point-of-care clinical decision support platform described herein, e.g., via a corresponding API (see for example the description with regard to FIG. 1 and/or FIG. 2). In an example implementation, the guideline platform facilitates the conversion of guideline documents into electronic navigable resources. As used herein, "guidelines" are decision tools, typically expressed as documents. In a medical context, guidelines are often comprehensive and complex documents that explain a disease and determine a best practice treatment regimens, often taking into account diagnosis, disease stage, medical technology, patient information, etc.

In some embodiments, a single document is transformed into a corresponding navigable resource. In other embodiments, two or more documents are combined and transformed into a navigable resource. In yet further embodiments, a single document is transformed into multiple navigable resources. Other combinations are possible within the spirit of the present disclosure. Typically, each guideline document is unstructured. In other embodiments, each document can be comprised of a combination of structured and unstructured sections.

Figure 3:
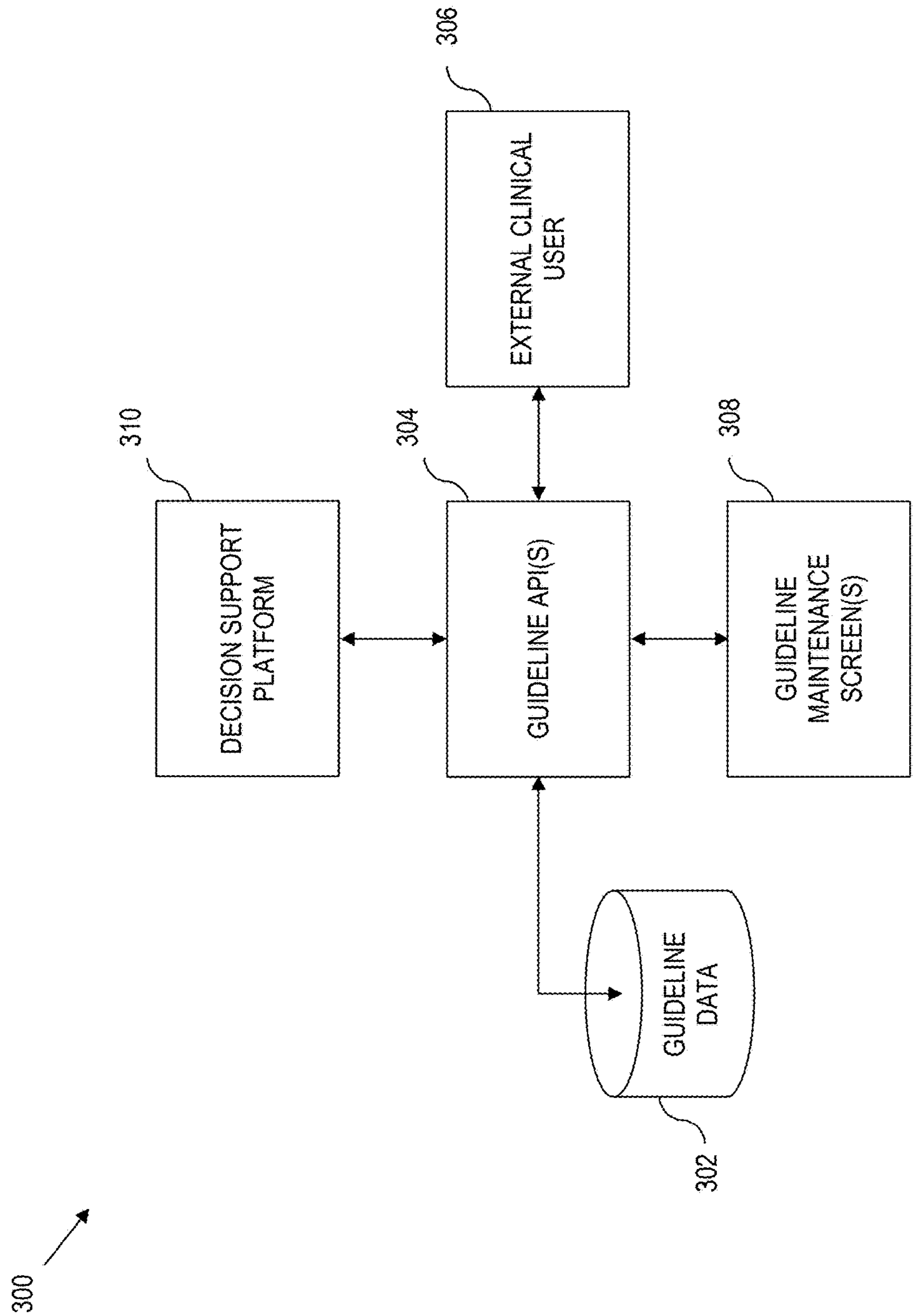
FIG. 3 is a block diagram illustrating a guideline component that can be integrated with the point-of-care clinical decision support platform of FIG. 1.

Referring now to FIG. 3, an example implementation illustrates a guideline platform 300. The guideline platform 300 comprises a guideline data source 302 and a Guideline API 304.

The guideline data source 302 is a computer-readable data source that stores guideline data. For instance, in an example embodiment, the guideline data stored in the guideline data source 302 comprises electronic navigable interactive guidelines, as will be described in greater detail herein. The guideline data source 302 can also store the underlying guideline documents that are used to create the electronic navigable interactive guidelines. In this regard, the underlying guideline documents can include electronic documents that represent guidelines, best practices, rules, medical information, and/or other resources. Such guideline documents are typically stored in document format such as PDF documents or text documents. In some instances, the underlying guideline documents can include jpegs or images, etc. Regardless, the underlying guideline documents serve as a source, or authority used to create one or more corresponding electronic navigable interactive guidelines.

The Guideline API 304 can in practice, include a graphical user interface that enables an end user to interact directly with the electronic navigable interactive guidelines stored in the guideline data source 302. For instance, as illustrated, an external clinical user interacting with the platform via a client computing device 306 can interface with an associated guideline API 304 to work with and interact with electronic navigable interactive guidelines. As a working example, the guideline API 304 can include one or more APIs that interface with third party computer resources, such as EMR partners, etc., e.g., via clinical screens that facilitate computer interaction with the guideline platform 300.

By way of illustration, a client device 306 (e.g., operated by an external clinical user) can make API calls to the Guideline API 304 to identify available electronic navigable interactive guidelines, to select guidelines, to start/access a select guideline, such as by identifying an identifier of a selected electronic navigable interactive guideline, to obtain guideline results given a position within the navigable guidelines, etc., examples of which are described in greater detail herein.

In some embodiments, the guideline platform 300 includes one or more guideline maintenance screens 308, e.g., graphical user interface screens that facilitate the ability to perform maintenance and/or version control on the guideline data. Maintenance and versioning are discussed in greater detail herein.

The Guideline API 304 can also and/or alternatively serve as an interface to a decision support platform 310 discussed in greater detail herein. In this regard, the guideline platform 300 can be implemented in the system 100 of FIG. 1.

In practice, the guideline data represents documents directed to best practices for the care of a patient. As a few practical examples, in the context of cancer treatment, the NCCN publishes documents that detail care for numerous types of cancer. The NCCN has numerous publications, each publication directed to a different type of cancer, where each document can be hundreds of pages in length. The shear volume of the material makes navigation and consultation of the documents tedious and prone to error. Moreover, since the documents are unstructured, it is difficult to locate a current status of a given patient along the patient's progression with a cancer treatment.

In practice, the present disclosure is not limited to conversion of NCCN documents into electronic navigable interactive guidelines. Rather, other guidelines, standards, etc., including payer guidelines, public, private, local, regional, national, and international guidelines can be converted into electronic navigable interactive guidelines.

Moreover, in some embodiments, the guideline platform 300 can be a stand-alone computer product. In other embodiments, the guideline platform 300 can be implemented within the architecture of the system of FIG. 1. In this regard, the guideline platform 300 can be implemented by the navigable component guidelines process 112 called by the API component 106. In other embodiments, such as where all processing is carried out internal to the platform 102, or where the navigable guidelines process 112 is not available, the guideline platform 300 can be implemented by the model 118, information/variables process 120, user interface 104 or combinations thereof.

Figure 4:
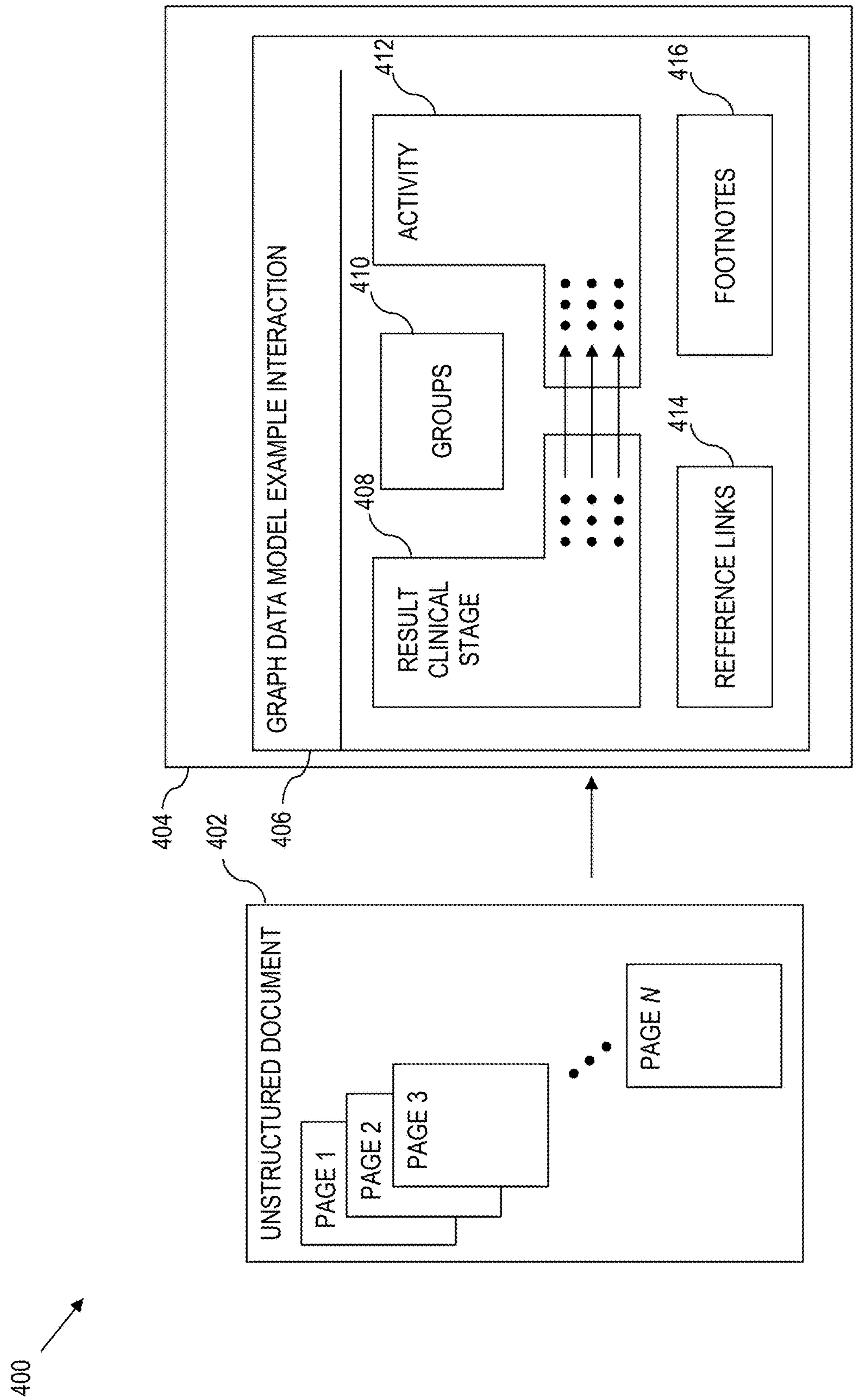
FIG. 4 is a schematic diagram illustrating an example of the conversion of a guideline into a graph data model.

Referring to FIG. 4, a schematic 400 illustrates the conversion of a guideline 402, e.g., NCCN cancer guideline, into a graph data model 404, by way of illustration and not by way of limitation. In the illustrated example, the guideline 402 includes potentially hundreds of pages of information, formatted into an unstructured PDF document. However, according to aspects herein, the unstructured document is converted into a model 404 that comprises a set of graph data relationships 406 (only one example graph data relationship illustrated for clarity of disclosure). Each graph data relationship 406 in a corresponding model 404 extracts relevant information from the guideline data 402. Here, the set of graph data relationships 406 are subsequently used to create navigable interactive guidelines, as described in greater detail herein.

Solely for sake of illustration, an example graph data relationship 406 illustrates that data from the corresponding guideline document 402 is extracted into a result 408, one or more activity groups 410, one or more activities 412, one or more supplemental reference links 414, and one or more footnote references 416.

To more clearly illustrate this example, reference is drawn to an NCCN Breast Cancer Guideline (however, as noted above, other guidelines or combination of guidelines may be used). See for example, NCCN Guidelines Version 5.2020 Invasive Breast Cancer Clinical State Chart page BINV-1 (page 15/239 of the pdf). In practice, the graph data relationship 406 illustrates only one of potentially numerous relationships 406 that are generated and integrated into a model 404 for an associated guideline 402.

In some embodiments, the graph data model is stored as a user navigable model, e.g., by creating database records that represent nodes and pathways, i.e., links between adjacent nodes, which map out a corresponding guideline. Because each record tracks nodes and links, the model approach is interactive because a user, starting on any node, can navigate through the model by following links that constrain the node relationships.

Figure 5A:
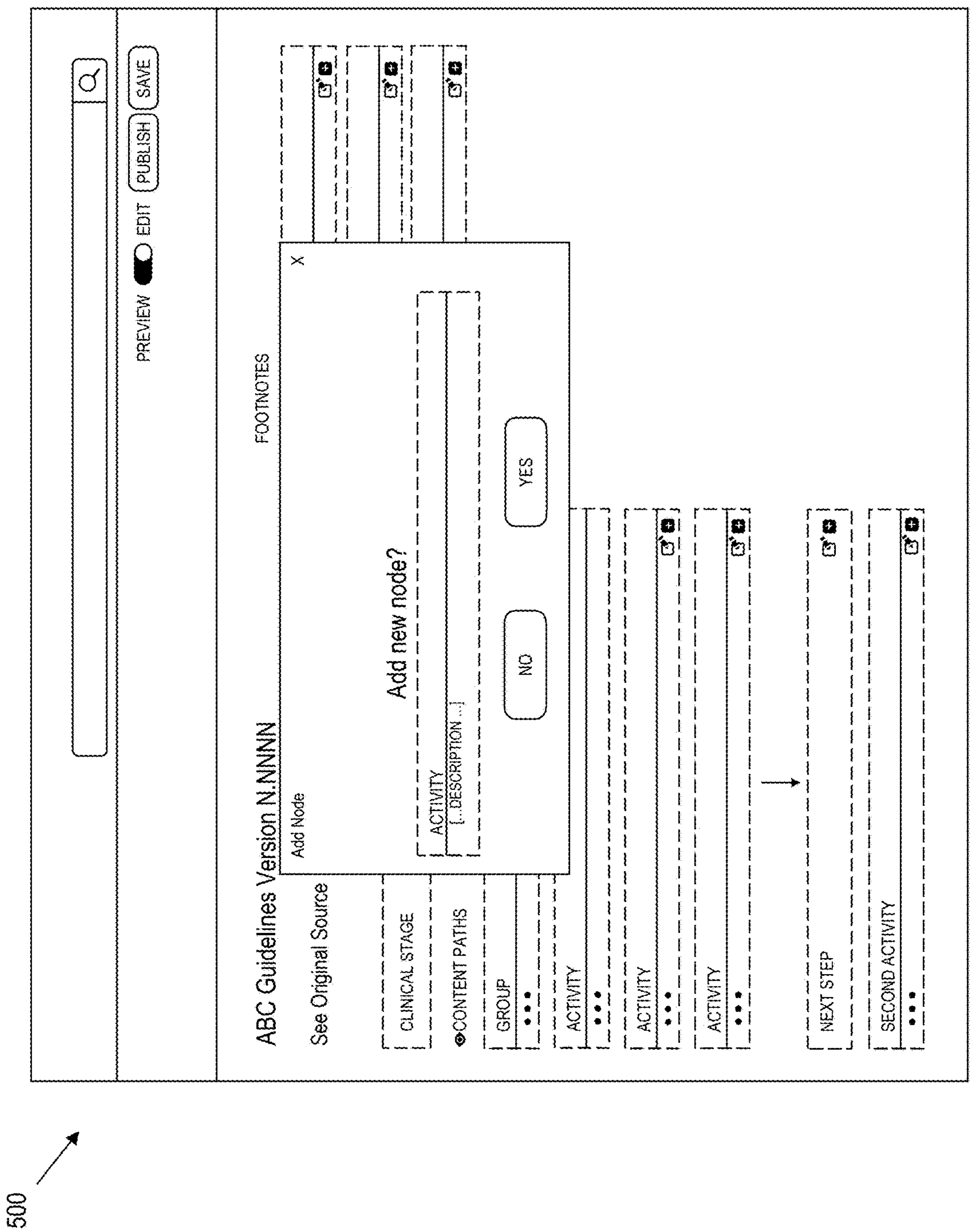
FIG. 5A is an example user interface screen illustrating a wizard to convert a guideline into a graph data model.

Referring to FIG. 5A, in some embodiments, models of guidelines are built using at least partial manual manipulation. In these embodiments, a wizard can be utilized to automate user interaction to recognize and assemble nodes and links. FIG. 5A illustrates an example wizard interface 500 for adding a new node to a model of a guideline (e.g., to build a graph data relationship as described with reference to FIG. 4).

As illustrated in FIG. 5A, a dialog box presents a user with an opportunity to input information (e.g., add a new node as illustrated), and optionally, to make some selections, add descriptions, edit parameters, etc. The user can also input or modify information such as a clinical stage, group, activity, next step, next activity, etc. At each entry of the wizard 500, the user can utilize the wizard dialog boxes to control the flow of data gathering to limit the inputs to manageable levels. Moreover, in some embodiments, the original document can be referenced to ensure that the automated guideline tracks with the actual source document. When the user is finished, the user has options via the wizard 500 to save, publish, preview, etc., the entries. Moreover, a search feature can be provided so that the user can find key information, e.g., to edit, revise, add, etc.

Figure 5B:
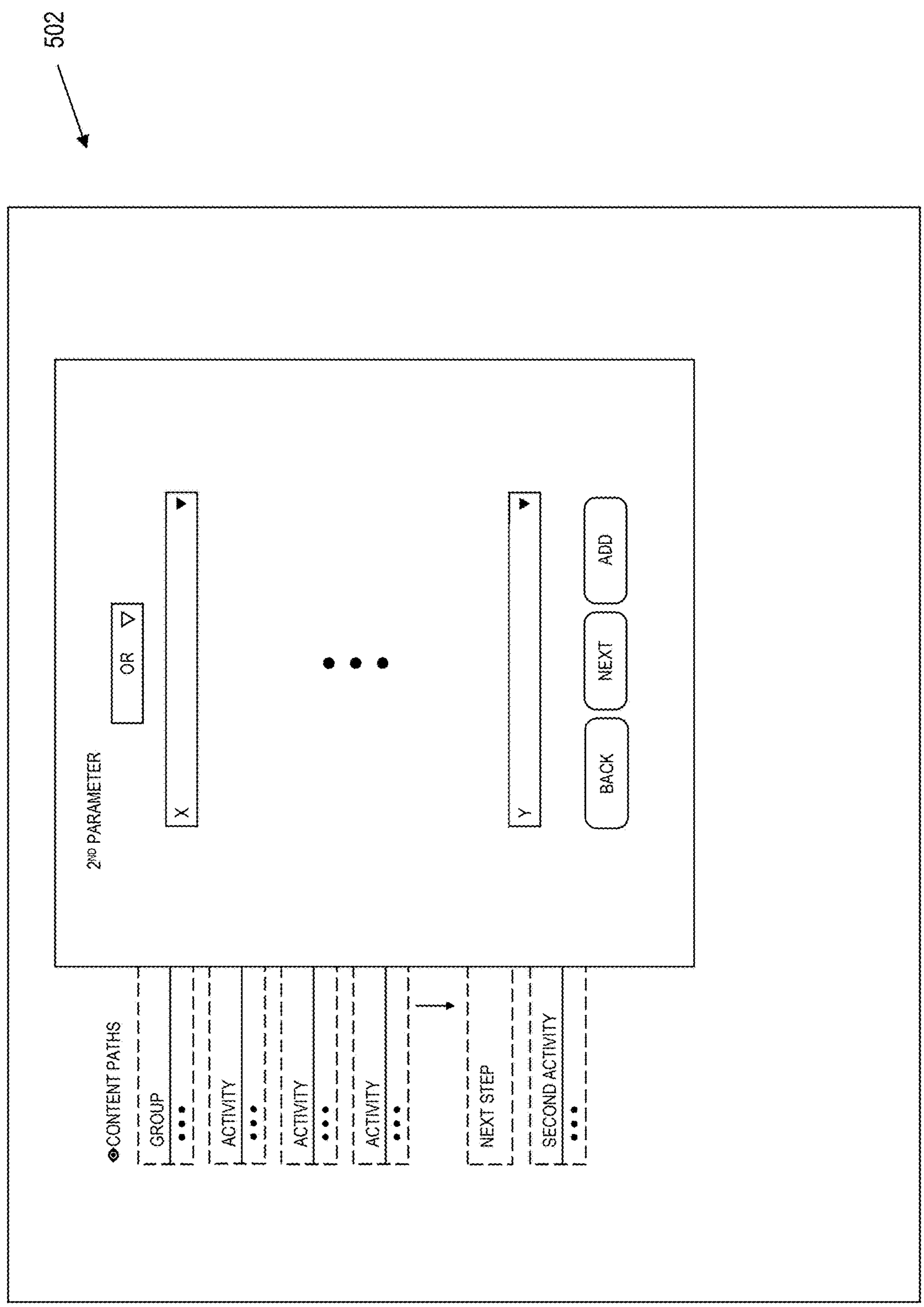
FIG. 5B is another example user interface screen illustrating a wizard to convert a guideline into a graph data model.

Referring to FIG. 5B, a second example wizard screen 502 illustrates an example approach to form links and node relationships (e.g., to build a graph data relationship as described with reference to FIG. 4). In the illustrated example, the user uses a dialog box to enter relevant information, e.g., by setting parameters, conditions, rules, or other data that transform the source data into a corresponding model form.

With reference to FIG. 3-FIG. 5B generally, by way of example, a computer-implemented process is provided to convert documents into electronic navigable interactive guidelines e.g., by converting the guideline into a model form, and coupling the model to a user navigable interface.

More specifically, in an example embodiment, the process is carried out by retrieving, by a computing device, an electronic document that defines a guideline (e.g., see guideline 402-FIG. 4) to be followed. The process then implements computer instructions for creating a graph data model (e.g., model 404, FIG. 4) for the associated guideline (guideline 402, FIG. 4). To create a model, the process implements computer instructions for establishing a set of pre-defined node types that characterize evaluation points for the guideline, and establishing for each predefined node type, at least one input, at least one output, or both at least one input and at least one output, where each output maps to a corresponding input of another instance of a node type.

An example implementation of a graph data relationship can identify example node types as "Result", "Activity Groups", "Activity", "Reference Links", and "Footnotes". When the guideline is converted into a model, the guideline is traversed to extract guideline requirement (e.g., actions, pathways, checklists, steps, etc.). Each guideline requirement entered into the model is associated with a node that is defined as an instance of one of the available node types. Links are then provided, designating input(s) and/or output(s) to the designated node. Here, the input(s) and/or output(s) can also be assigned based upon pre-defined link relationships, examples of which are described below.

The process then implements computer instructions for creating a model of the guideline by performing in an iterative manner, parsing the electronic document to select a next detected guideline requirement, mapping the selected guideline requirement to a matching node type to define a guideline node, and assigning at least one input or output associated with the guideline node based upon the guideline requirement specified in the electronic document. Once the model is created, the process implements computer instructions for storing the graph data model as an electronic navigable interactive guideline in a data storage device.

In further embodiments, the electronic navigable interactive guideline is visually represented as a navigable graph by rendering the graph data model in a graphical user interface using a visual metaphor to graphically represent the nodes and corresponding links.

Figure 6:
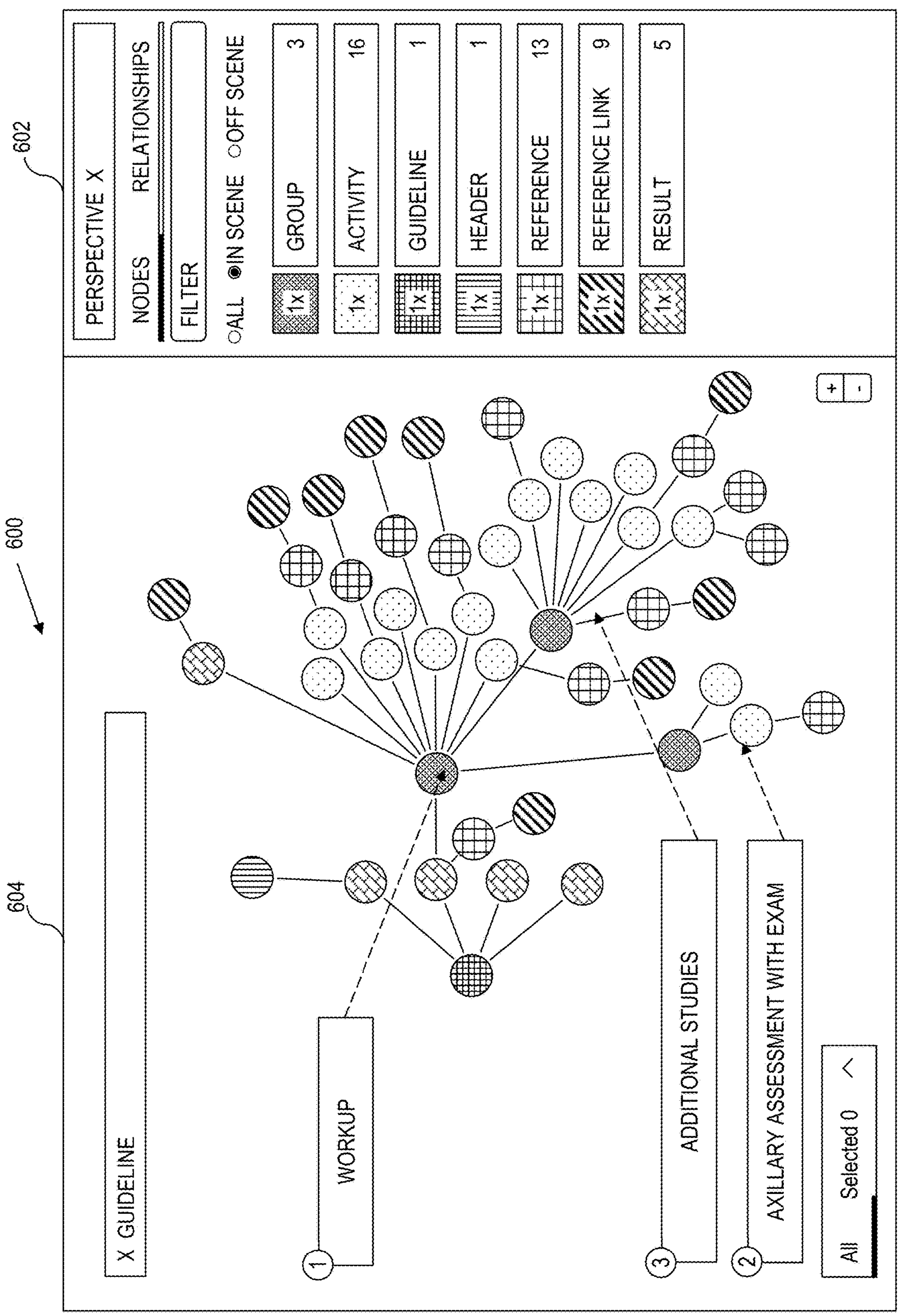
FIG. 6 is an example user interface screen that provides a graphical representation of graph data model nodes and relationships defining an electronic navigable interactive guideline.

Referring to FIG. 6, an example navigable graph 600 is illustrated. The navigable graph 600 can be integrated into the system 100 of FIG. 1.

In this non-limiting example, all clinical pathways defined in the guideline are visualized with visual metaphors (e.g., color-coded circles), whereas relevant data is stored in the corresponding model, which may be recalled and displayed in a separate view.

The visual graph enables the entire guideline (or portions thereof) to be visualized. Moreover, nodes and node relationships are visually and graphically presented. In this regard, zoom and/or paging preferences can be provided to navigate relatively complex graphical representations such that any given screen may illustrate all or a portion of the navigable graph.

The example navigable graph 600 includes a legend 602 that identifies example node types (e.g., Group, Activity, Guideline, Header, Reference, Reference Link, and Result). Each has a unique shading matched to associated nodes in a node graph view 604 so that node types are visually represented in the graph within the node graph view 604. In practical applications, the graph can utilize at least one of color, size, shape, etc., to represent each node in the graphical representation. The legend 602 can also include other relevant data to assist in the usability of the visualization, such as node type counts, references to the guideline visualized, sort and filter options to show or hide certain nodes or relationships, etc. Of course, the exact medical condition will ultimately affect the node types/node definitions.

As noted above, according to some aspects of the present disclosure, the graph data model can be even more flexible by assigning node relationship rules to the links that interconnect nodes. By way of non-limiting example, each node can have zero or more inputs, and zero or more outputs, in any combination.

Constraining the nodes and node relationships through a concise set of rules that can be mapped using a limited number of link relationships assists in generating clean graphs that accurately portray journey tracking in a manner that makes consumption easy and extensible.

The approach herein also improves the performance of computing systems by converting unstructured documents into structured graph data models that consolidates and organizes large quantities of information (including repetitive information found in the unstructured documents) into navigable visual metaphors that represent treatment progressions. Thus, an entire guideline, which may require hundreds of pages of data, can be visualized, potentially in a single node graph view 604. This saves memory because only relevant portions of the guideline have to be loaded, rather than loading the entire guideline.

Maintenance/Versioning

The computer-implemented process can implement computer instructions for creating a model of the guideline in a first computing environment (e.g., a maintenance/versioning environment), and storing the graph data model as an electronic navigable interactive guideline in a first database in the first computing environment. The computer-implemented process can also implement computer code for publishing the electronic navigable interactive guideline to second database in a second computing environment (e.g., a production environment), such that the electronic navigable interactive guideline is accessible by a client computing device interacting with the second computing environment. In some embodiments, publishing the electronic navigable interactive guideline to second database in a second computing environment comprises publishing the electronic navigable interactive guideline utilizing a user role-based authorization to electronically verify that the created electronic navigable interactive guideline is authorized for publication to the production environment, and not publishing the electronic navigable interactive guideline where a predetermined requirement of the user role based authorization is not satisfied. Also, in some embodiments, publishing the electronic navigable interactive guideline to second database in a second computing environment comprises publishing a new version of the electronic navigable interactive guideline to the second database to replace a previous version of the electronic navigable interactive guideline, and moving the previous version of the electronic navigable interactive guideline to an archive guideline database on the production environment.

Figure 7:
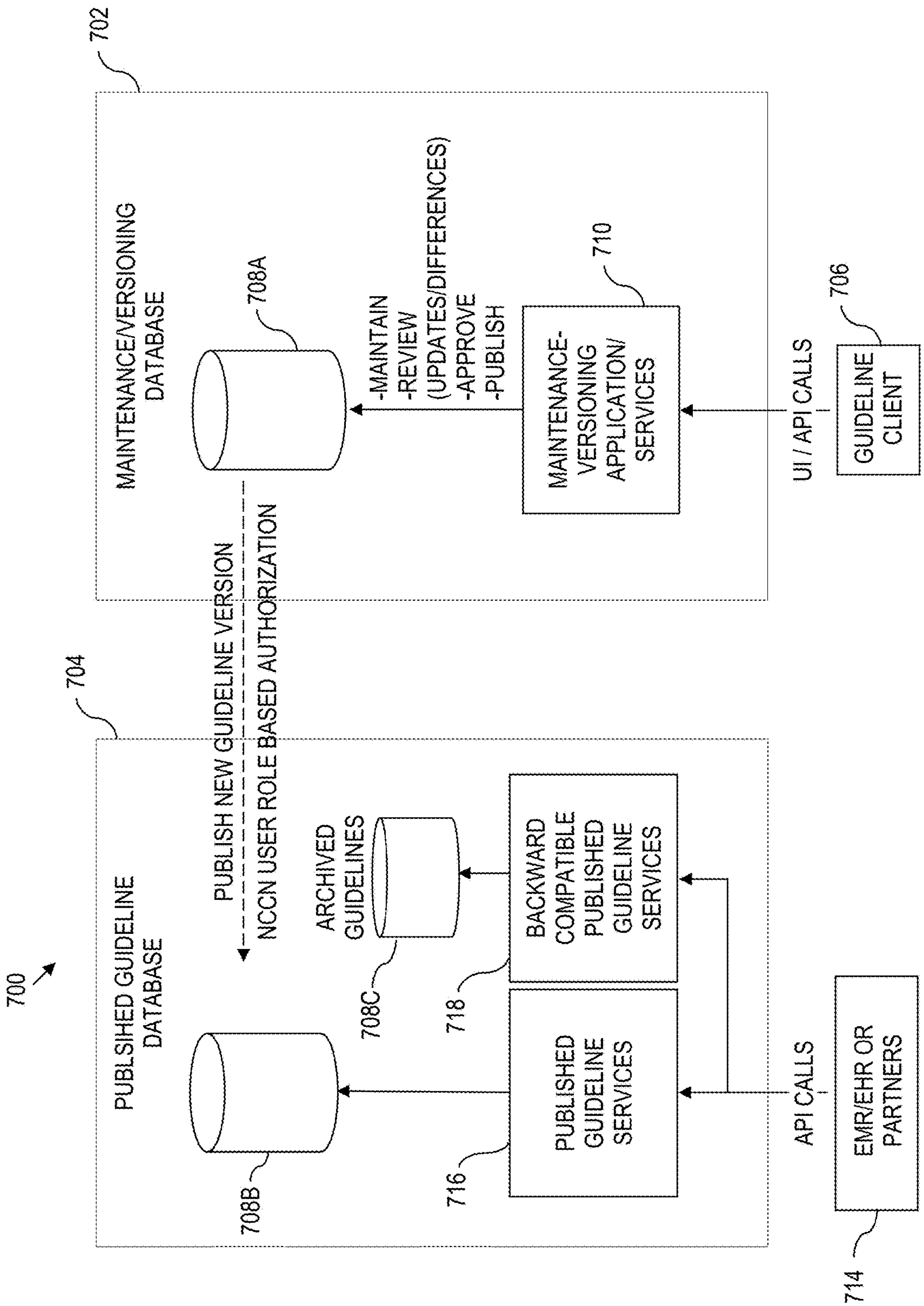
FIG. 7 illustrates an example maintenance/versioning environment and a production environment for managing electronic navigable interactive guidelines.

By way of an illustrative example, referring to FIG. 7, because underlying guidelines can change, aspects of the present disclosure provide a graph data model maintenance/versioning process that enables guidelines that have been converted to electronic navigable interactive guidelines to be updated so as to track updates, revisions, changes, and other refreshes to underlying guidelines.

As illustrated in FIG. 7, aspects of the present disclosure provide a version control platform 700 that includes a maintenance/versioning environment 702 and a production environment 704. In some embodiments, the version control platform 700 can be integrated into the system 100 of FIG. 1.

In practical applications, the maintenance/versioning environment 702 can create and update the electronic navigable interactive guidelines. Once a relevant electronic navigable interactive guideline is approved (e.g., undergone testing, evaluation for cyber vulnerabilities and security screening, debugging, optimizing, etc., an instance of the appropriately approved electronic navigable interactive guideline can be moved from the maintenance/versioning environment 702 to the production environment 704. Once on the production environment 704, the electronic navigable interactive guideline is implemented as live data that can be interacted with by end users.

Turning initially to the maintenance/versioning environment 702, one or more client computers 706 interacts with guidelines stored in a maintenance/versioning data source 708A. To ensure consistent and controlled interaction, a client computer 706 can interact with the maintenance/versioning environment 702 using a user interface (UI) and/or a series of provided API calls. In practical applications, the maintenance/versioning environment 702 can be used to create the electronic navigable interactive guideline as described more fully herein.

For instance, as illustrated, the client computer 706 interacts with a process 710 (e.g., an application, service, etc.) to carry out maintenance and/or versioning of a guideline. Interaction can be carried out to implement bug fixes, changes to one or more navigable paths, to carry forward changes to the underlying guideline, to expand features/capabilities of an associated electronic navigable interactive guideline.

Once an electronic navigable interactive guideline has been approved on the maintenance/versioning platform 702, a publish process publishes an instance of the updated electronic navigable interactive guideline to the production environment 704. In some embodiments, a user-role based authorization is required before the update is published in the production environment 704.

In the example production environment 704, the platform includes an active/current data source 708B that stores the active instance of each electronic navigable interactive guideline. The production environment 704 can also include a legacy data source 712 that stores legacy instances of the electronic navigable interactive guidelines. For instance, the production environment 704 may update or otherwise a provide access to legacy data because the treating medical point-of-care individual has not moved to the latest prevailing treatment options.

In this regard, a client 714 can be an end user (external clinical user), e.g., a point-of-care medical practitioner that is attending to a patient. The client 714 interacts with the production environment 704, e.g., via suitable API calls to a published guideline service 716 to interact with the most up to date electronic navigable interactive guidelines via the data source 708B. Analogously, the client 714 interacts with the production environment 704, e.g., via suitable API calls to a backward compatible published guideline service 718 to interact with the most up to date electronic navigable interactive guidelines via the data source 708C.

In practical applications, the API on the production environment 704 can be designed with simple API calls to facilitate interaction by medical practitioners interacting with client devices. 714. For instance, HTTP GET commands can be used to identify available guidelines, select a guideline, respond with a start of a guideline, respond with results given a position within a guideline, etc.

As a few illustrative examples using GET endpoints, the API can be utilized to identify available guidelines (e.g., /guidelines/to receive a response back containing result for all the available guidelines). In a practical application, the computer code can return for each guideline, an identifier, label, type, long description, short description, version number, and other relevant information for the client processing device to discern the relevant guidelines for interaction with the API.

As another non-limiting but illustrative example, the API can respond with a start of a guideline (e.g., /guideline/<<guildeLineID>>/nextstep) to receive a response back. As yet another non-limiting example, the API can provide a respond with results given a position within a guideline (e.g., /guideline/<<guildeLineID>>/<<currentStepID>>/nextstep) to receive a response back result for the next steps from current step identifier, etc.

Example Clinician Interaction with a Model of a Guideline

Figure 8:
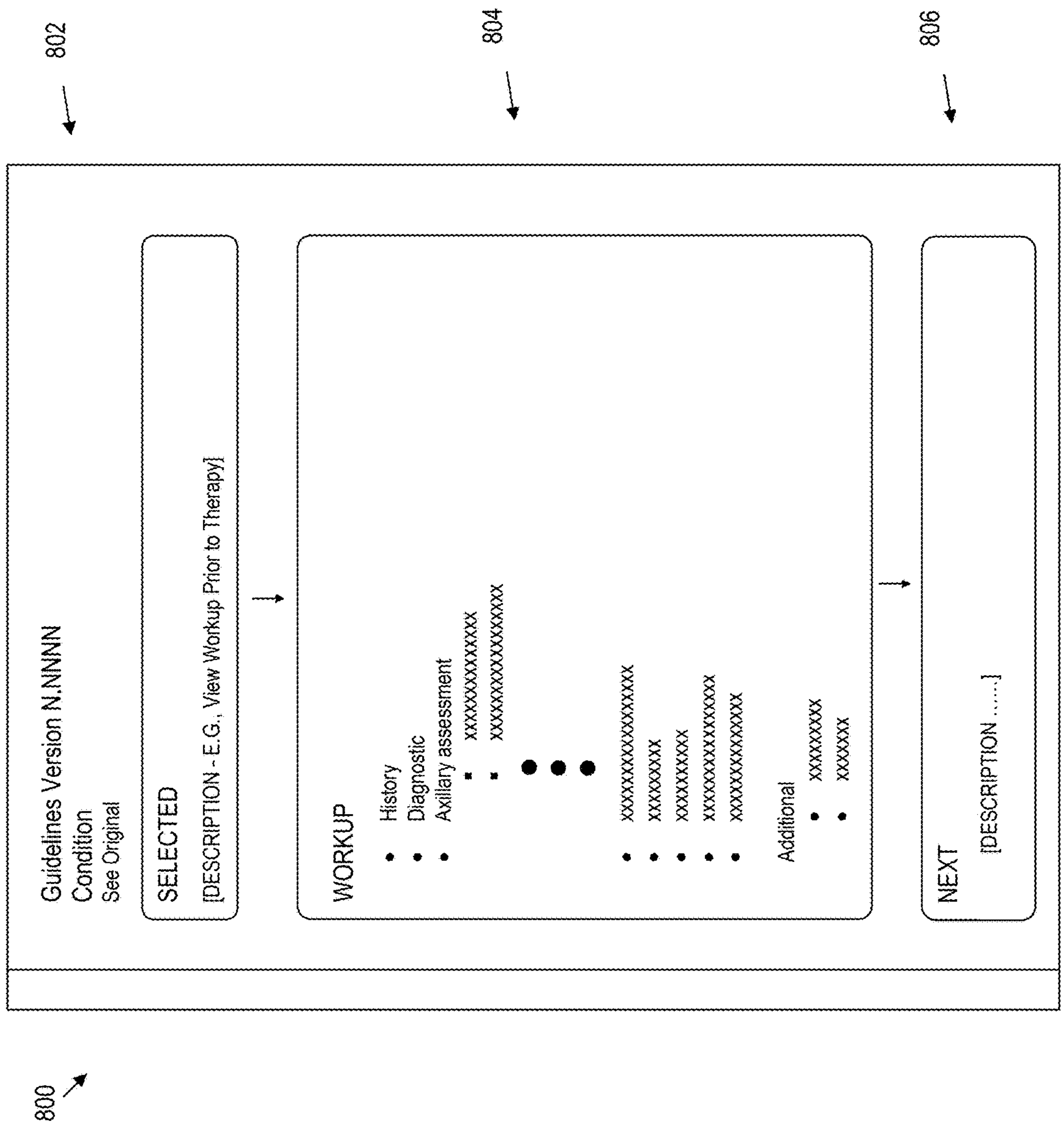
FIG. 8 is an example user interface screen showing a clinician navigating through an electronic navigable interactive guideline.

Referring to FIG. 8, an illustration of a graphical user interface 800 shows a screen that presents an interaction with an example electronic navigable interactive guideline (e.g., a model built using the NCCN breast cancer guideline for sake of illustration). The graphical user interface 800 can be integrated into the system 100 of FIG. 1.

The graphical user interface 800 illustrates a data region 802, showing the guideline that was modeled, the current patient position along a pathway in the guideline region 804, and an action region 806.

Because of the simplified design of the interactive node/link relationships, the client user experience can be enhanced with a user interface that utilizes the relationships to lay our content. Here, quick navigation is possible by using the nodes and directed pathways to simplify where the user can make a selection (e.g., by positioning response requirements to a common screen location (e.g., action region 806, located at the bottom section of the screen, etc.). In some embodiments, abilities can also be provided to highlight and/or skip guideline nodes, e.g., based upon clinical parameters. The reference links can be positioned in-line.

Further, in some embodiments, because the electronic navigable interactive guideline is an interpretation of a documented guideline, a link can be provided to the source guideline for reconciliation, auditing, and insights that are not covered by the interactive guideline.

Figure 9:
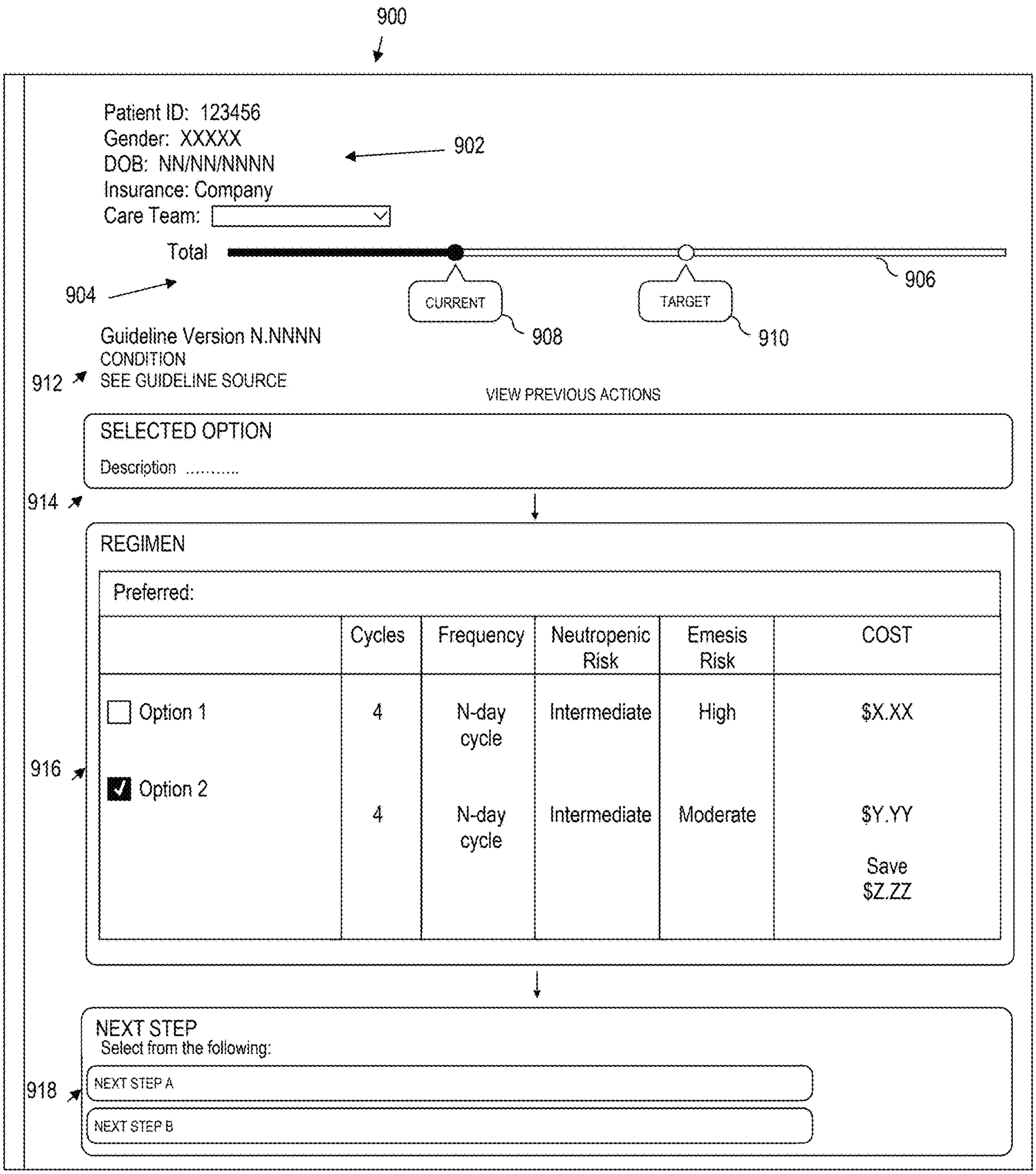
FIG. 9 is another example user interface screen showing a clinician navigating through an electronic navigable interactive guideline.

Referring briefly to FIG. 9, as noted in greater detail with reference to FIG. 1 and FIG. 2, when integrated with the platform 102, APIs can be used to integrate cost data, AI-based risk assessment data, etc.

By way of illustration, FIG. 9 may thus illustrate an example detail of a node in a model of a guideline (e.g., NCCN breast cancer guideline) where the best practice recommended by the NCCN is reconciled with cost of care information. In other embodiments, FIG. 9 may be implemented as a page within a clinician portal.

As illustrated, an example interface 900 includes several sections. A first section 902 provides basic patent information, such as a patient ID, gender, date of birth, insurance company information, etc. The platform 102 (FIG. 1) can pull the information presented in the first section 902, e.g., by accessing EMR records. When implemented as an open platform with extensible API, the platform can use the Internet, e.g., via service calls, etc., to access EMR records from an EMR records provider.

A second section defines a running cost section 904 provides a bar line 906 that tracks a current total 908 against a target total 910. This allows the clinician to see in a quick snapshot how the progression of patient care is going. In some embodiments, the target 910 is defined based upon the performance tuning that is implemented specific to the patient (e.g., by tuning patent care for quality of care, time, financial cost, a combination thereof, etc., as described more fully herein. In some embodiments, the running cost section 904 can show value-based cost from a historical perspective (e.g., date range, to date, etc.). In other embodiments, the running cost section 904 can show cost for the current period, e.g., current clinician visit. In other embodiments, the running cost section 904 can show a prediction of total cost, cost over a window of time, or any combination of the above.

A third section 912 is a reference section that identifies the underlying source, justification, attribution, or other support references to establish the clinical pathway and clarify where in the progression, the patient is currently situated.

A fourth section 914 provides a description of the selected option of patient care in the pathway associated with that patient. The fourth section is pulled from the reference defined in the third section 912.

A fifth section 916 provides a regimen section. In this example configuration, the interface provides a regimen, e.g., according to the navigable guideline (e.g., as optionally tweaked by the performance tuning). Moreover, in some embodiments, the interface can provide alternatives. This allows the clinician to select a regimen based upon a number of factors. In the illustrated example, the regimen screen includes cycles, frequency, risks, and cost. This allows the clinician to tune the patient care based upon a complete vison of risk, cost, burden, and other factors.

In some embodiments, the clinician's selection of a regimen option functions as a navigable input into a navigable guideline, thus charting a patient progression through a treatment plan.

In some embodiments, the screen can also present a sixth section 918, which presents future items, such as the next steps. Here, the next steps can be derived from the navigable guidelines, as described more fully herein.

Practices that participate in value-based payment models are typically engaged in one-sided or two-sided risk arrangements. In these risk arrangements, the target price of an episode is often set based on a number of patient-specific conditions, such as illness type and comorbidities. Clinicians and administrators have been challenged to find effective ways to track costs of care to inform decisions and predict financial performance in these models. With these challenges in mind, the platform described with reference to the FIGURES herein, helps clinicians predict the cost of care, at the onset of an episode, and accurately track costs throughout the episode of care. These unique insights enable physicians/clinicians to make more informed treatment decisions and gain deeper visibility into value-based performance.

For instance, as illustrated throughout the disclosure herein, the platform enables practices to both measure up-to-date care expenses and predict value-based performance, view an accurate view of episode costs, at any point in a progression of client care. By tracking in-practice costs as they occur, physicians and administrators can identify and address outliers, and also pinpoint when specific costs are trending above target for a particular patient. The platform herein is further positioned to provide close monitoring of at-risk patients, to deliver customized patient interventions, e.g., for palliative or hospice care, etc.

In some embodiments, aspects herein improve the technology of computer systems by leveraging APIs to create maps, and then plot navigable pathways through the created maps by blending and tuning parameters from discrete and unrelated data sources.

For instance, the "interactive" nature of the model is clearly illustrated because the clinician can select within the "Regimen" section. By integrating cost information and optionally, AI-based risk analysis (e.g., addressing biosimilars, alternatives, etc.), a pathway can include options that the clinician can follow that provides equivalent quality of care, while bringing about an improved (lower) cost of care. Thus, the illustrated model not only characterizes a guideline, but also captures and saves a forensic record that will allow a clinician to retrospect a patient history to see where the guideline was followed, where the guideline was deviated from, and attributions that explain why the guideline was followed or not followed.

Miscellaneous

As noted more fully herein, the disclosed clinical decision support platform is a solution that assists medical personnel, e.g., oncologists, specialist, etc., with matching the patient to the appropriate treatment based on adherence to prescribed guidelines (e.g., NCCN guidelines in the example application of cancer treatment). However, aspects herein also consider value. Once a treatment is selected, the clinical decision support platform identifies when the episode of care starts for the patient and can provide financial estimates of total cost. As care is delivered, within the practice and outside of the practice, care navigators can use the clinical decision support platform to monitor adherence to guidelines and track cost reconciled against the original estimate. Machine learning/AI technology can further be used to identify patients that are at risk and propose interventions. Practice level analytics enables practice administrators and directors of quality/value-based care to track guideline adherence across the practice and monitor costs across their patient population.

In this regard, certain aspects of the clinical decision support platform combine the digitization and navigation of guidelines, integrate a total cost of care and further integrate artificial intelligence for predicting, planning and carrying out interventions, e.g., by using built-in components, or by leveraging APIs to enable third party partners.

Notably, the platform improves data management and computer processing by enabling third-party integration and constraining third-party interaction through defined APIs, which can handle data translation, mapping and other compatibility matters, improving processing and data integrity.

As a result of the combination of features herein, lower cost of care is realized. Moreover, adherence to guidelines increases due to improved usability of the guidelines. For instance, as noted in greater detail herein, when evaluating next steps for treatment for a patient given a diagnosed medical condition, the appropriate guideline essentially walks the clinician through appropriate selections avoiding the need to read through potentially hundreds of pages to figure out the right choice for the patient.

Computer System Overview

Figure 10:
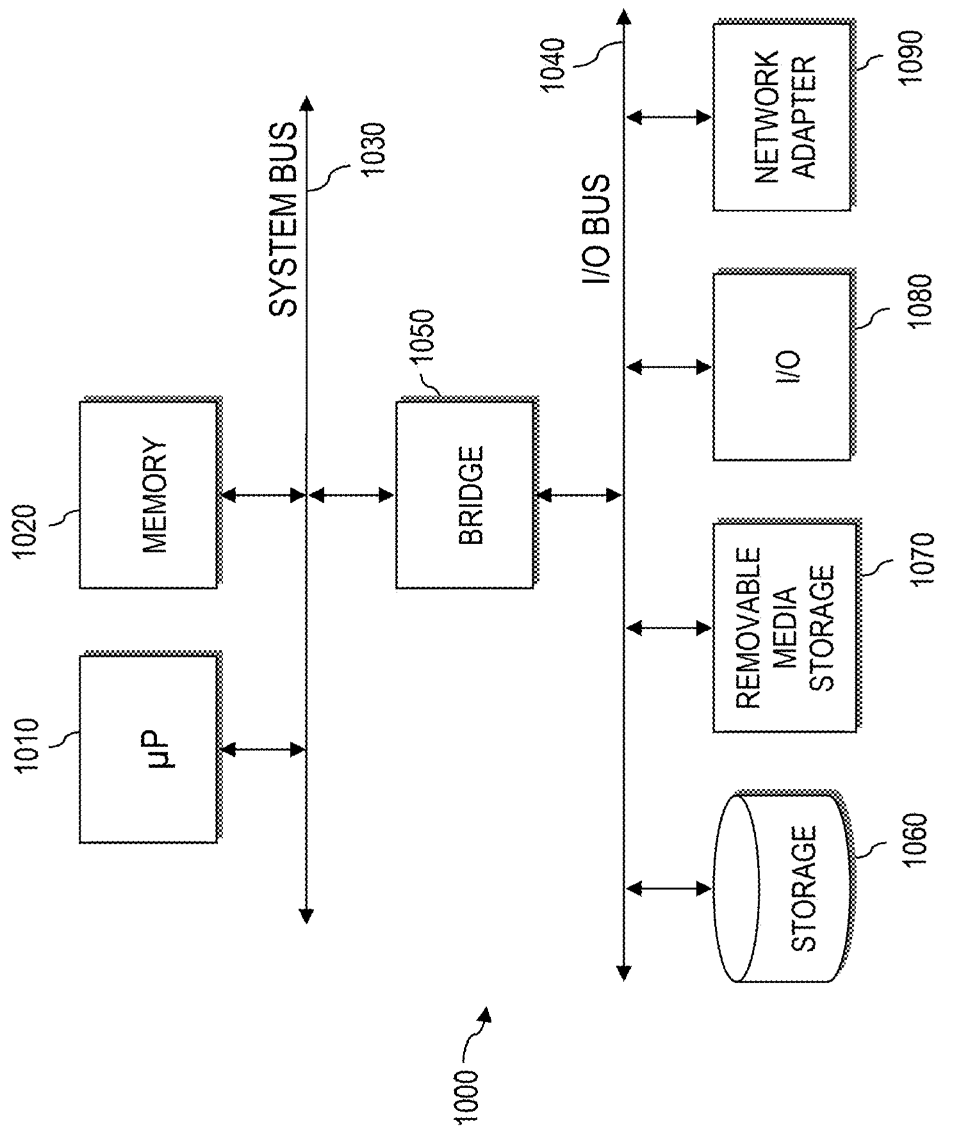
FIG. 10 is an example computer architecture that is suitable for execution of the platform, systems and methods described herein.

Referring to FIG. 10, a schematic block diagram illustrates an exemplary computer system 1000 for implementing the various methods described herein, e.g., by interacting with a user. The exemplary computer system 1000 includes one or more microprocessors (P) 1010 and corresponding memory 1020 (e.g., random access memory and/or read only memory) that are connected to a system bus 1030. Information can be passed between the system bus 1030 and bus 1040 by a suitable bridge 1050. The bus 1040 is used to interface peripherals with the one or more microprocessors (P) 1010, such as storage 1060 (e.g., hard disk drives); removable media storage devices 1070 (e.g., flash drives, DVD-ROM drives, CD-ROM drives, floppy drives, etc.); I/O devices 1080 (e.g., mouse, keyboard, monitor, printer, scanner, etc.); and a network adapter 1090. The above list of peripherals is presented by way of illustration and is not intended to be limiting. Other peripheral devices may be suitably integrated into the computer system 1000.

The microprocessor(s) 1010 controls operation of the exemplary computer system 1000. Moreover, one or more of the microprocessor(s) 1010 execute computer readable code (instructions), that instructs the microprocessor(s) 1010 to implement the methods, systems, and other computer-implemented aspects set out and described herein with regard to FIG. 1-FIG. 9. herein. The computer readable code may be stored for instance, in the memory 1020, storage 1060, removable media storage device 1070 or other suitable tangible storage medium accessible by the microprocessor(s) 1010. The memory 1020 can also function as a working memory, e.g., to store data, an operating system, etc.

Thus, the exemplary computer system 1000 or components thereof can implement methods and computer-readable storage devices as set out in greater detail herein. Other computer configurations may also implement the methods and computer-readable storage devices as set out in greater detail herein. Computer program code for carrying out operations for aspects of the present invention may be written in any combination of one or more programming languages. The program code may execute entirely on the computer system 1000, partly on the computer system 1000, partly on the computer system 1000 and partly on a remote computer or entirely on a remote computer or server. In the latter scenario, the remote computer may be connected to the computer system 1000 through any type of network connection, e.g., using the network adapter 1090 of the computer system 1000.

Aspects of the present invention are described herein with reference to flowchart illustrations of methods and computer program products according to embodiments of the invention. Each block of the flowchart illustrations can be implemented by computer program instructions. These computer program instructions may be provided to a processor to produce a machine, such that the instructions, which execute via the processor of the computer or other programmable data processing apparatus, create means for implementing the functions/acts specified in the flowchart.

These computer program instructions may also be stored in a computer readable storage medium (i.e., computer readable storage device) such that the instructions stored in the computer readable medium produce an article of manufacture including instructions, which implement the function/act specified in the flowcharts when implemented by a processor.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely of hardware, entirely software (including firmware, resident software, micro-code, etc.) or combining software and hardware implementation. Any combination of one or more computer readable media may be utilized. Aspects herein may be implemented either as a computer readable storage medium or a computer readable signal medium. A storage medium is a tangible or otherwise physical memory, e.g., a storage device. A computer readable signal medium may include a propagated data signal per se, with computer readable program code embodied therein, for example, in baseband or as part of a carrier wave. A computer readable signal medium may be any computer readable medium that is not a computer readable storage medium and that can communicate, propagate, or transport a program for use by or in connection with an instruction execution system, apparatus, or device.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description but is not intended to be exhaustive or limited to the invention in the form disclosed. Many modifications and variations will be apparent to those of ordinary skill in the art without departing from the scope and spirit of the invention.

Having thus described the invention of the present application in detail and by reference to embodiments thereof, it will be apparent that modifications and variations are possible without departing from the scope of the invention defined in the appended claims.

What is claimed is:

1. A medical decision system, the system comprising:

a computer-implemented platform that carries out computer program code to:

electronically extract electronic medical record information associated with a patient receiving medical care from at least one medical records data source;

output to a graphical user interface, an electronic guideline, where:

the electronic guideline is selected based upon at least one of an identification of the patient receiving medical care or selected information from the extracted electronic medical record information; and the graphical user interface facilitates navigation of the electronic guideline;

store a value for a tuning parameter that affects clinical decision making, where the value for the tuning parameter is determined based upon at least one of: the identification of the patient receiving medical care, the extracted electronic medical record information, or information extracted from the electronic guideline; and output to a first display screen, a generated clinical pathway, where the generated clinical pathway comprises a customized, clinical pathway for the patient receiving medical care using the value of the tuning parameter, wherein the generated clinical pathway recommends a future clinical service for the patient receiving medical care, and the clinical pathway is reconciled with actual costs of care extracted from electronically retrieved cost information.

2. The system of claim 1, where the platform further carries out program code to:

output an interface that allows the user to manually specify at least one of the tuning parameter or the value of the tuning parameter.

3. The system of claim 1, wherein:

the tuning parameter corresponds to biosimilar substitution and the value of the tuning parameter corresponds to a pre-programmed, default substitute biosimilar that is automatically substituted by the platform against a corresponding biologic.

4. The system of claim 1, wherein:

the electronic guideline comprises a select one of a payer guideline or an insurance guideline; and the customized clinical pathway for the patient receiving medical care includes a biosimilar that is extracted from the electronic guideline.

5. The system of claim 1, wherein:

the output to the first display screen comprises indicia designating at least two user-selectable options, where a first one of the options corresponds to a first regimen at a first cost and the second one of the options corresponds to a second regimen at a second cost that is different to the first cost.

6. The system of claim 5, wherein:

the platform interacts with a risk assessment engine that outputs for each of the at least two user-selectable options, at least one risk assessment for the associated regimen.

7. The system of claim 1, wherein the tuning parameter affects the clinical pathway based upon at least one of time, treatment, risk assessment, patient-profile similarity, patient profile differences, extraction of data from one or more electronic guidelines, or a trajectory to transition an out-of-guideline patient into a selected electronic guideline.

8. The system of claim 1, wherein the tuning parameter affects the clinical pathway based upon individualized cost.

9. The system of claim 1, wherein the tuning parameter affects the clinical pathway based upon at least one of: cost for a next step in treatment, cost for a particular treatment, cost based upon treatment for a period, cost based upon total treatment.

10. The system of claim 1, wherein:

the platform outputs a prediction of future costs based upon at least one of:

future events in the generated clinical pathway; or detected changes representing a diversion in a treatment regimen defined by the generated clinical pathway.

11. The system of claim 1, wherein the platform further carries out program code to:

perform compliance monitoring of the patient receiving medical care by tracking progress of the patient relative to the generated clinical pathway; and output at least one of:

a message indicating the patient remains on the clinical pathway; and a message indicating that the patient has deviated from the clinical pathway.

12. The system of claim 1, wherein the platform further carries out program code to:

output an interface that enables the user to select or modify a current value of the tuning parameter; and interact with a model component that generates a model that models possible outcomes for the patient receiving medical care by following the clinical pathway based upon a current value of the tuning parameter.

13. The system of claim 1, wherein:

the user comprises a clinician; and the platform further carries out program code to implement a first interface, wherein the clinician interacts with the first interface of the platform to evaluate cost of care to follow the clinical pathway based upon episode cost.

14. The system of claim 1, wherein:

the user comprises a clinician;

the platform further carries out program code to implement a first interface, wherein the clinician interacts with the first interface to track a progress of the patient receiving medical care as a function of adherence to the electronic guideline and/or to compare regimens generated as part of the clinical pathway.

15. The system of claim 1, wherein:

the electronic guideline comprises at least one of a payer guideline or an insurance guideline.

16. The system of claim 1, wherein:

the electronic guideline comprises a clinical treatment guideline.

17. The system of claim 1, wherein:

the platform further carries out program code to:

implement a guideline interface that generates the electronic guideline, the guideline interface configured to:

extract a guideline document;

parse the extracted guideline document to obtain a guideline; and convert the obtained guideline into graph data within a navigable guideline model.

18. The system of claim 17, wherein:

the future clinical service is determined by interacting with the electronic guideline via the navigable guideline model, to select the future clinical service as a node in the navigable guideline model.

19. The system of claim 18, wherein:

the graph data within the navigable guideline model includes at least two user selectable nodes;

user selection of a select one of the at least two user selectable nodes functions as a navigable input into the navigable electronic guideline so as to chart a patient progression through a treatment plan associated with the clinical pathway.

20. A computer-implemented process for building a care plan that is customized for a patient receiving medical care, comprising:

carrying out, by a computer-implemented platform, computer program code for:

electronically extracting electronic medical record information associated with the patient receiving medical care from at least one medical records data source;

outputting by a graphical user interface, an electronic guideline, where:

the electronic guideline is selected based upon at least one of an identification of the patient receiving medical care or selected information from the extracted electronic medical record information; and the graphical user interface facilitates navigation of the electronic guideline;

storing a value for a tuning parameter that affects clinical decision making, where the value for the tuning parameter is determined based upon at least one of: the identification of the patient receiving medical care, the extracted electronic medical record information, or information extracted from the electronic guideline;

outputting to a display screen, a generated clinical pathway for the patient receiving medical care using the value of the tuning parameter to custom tailor the care plan for the patient receiving medical care, wherein:

the generated clinical pathway recommends a future clinical service for the patient receiving medical care; and the clinical pathway is reconciled with actual costs of care extracted from electronically retrieved cost information.

21. The computer-implemented process of claim 20 further comprising:

outputting indicia designating at least two user-selectable options, where a first one of the options corresponds to a first regimen at a first cost and the second one of the options corresponds to a second regimen at a second cost that is different to the first cost.

22. The computer-implemented process of claim 20 further comprising:

providing an interface to enable a user to select the tuning parameter so as to affect the clinical pathway based upon at least one of cost, time, treatment, risk assessment, patient-profile similarity, patient profile differences, electronic guidelines, or a trajectory to transition an out-of-guideline patient into an electronic guideline.

23. The computer-implemented process of 20 further comprising:

generating the electronic guideline by:

extracting a document via the guideline interface;

parsing the extracted document to obtain a guideline; and converting the obtained guideline into graph data within a navigable guideline model; and recommending a future clinical service by interacting with the navigable guideline model to select the future clinical service as a node in the navigable guideline model.

* * * * *